US008735829B2

(12) United States Patent
Kuwabara

(10) Patent No.: US 8,735,829 B2
(45) Date of Patent: May 27, 2014

(54) RADIOGRAPHIC IMAGE CAPTURING SYSTEM, PROGRAM STORAGE MEDIUM, AND METHOD

(75) Inventor: Takeshi Kuwabara, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 26 days.

(21) Appl. No.: 13/427,136

(22) Filed: Mar. 22, 2012

(65) Prior Publication Data

US 2012/0241629 A1  Sep. 27, 2012

(30) Foreign Application Priority Data

Mar. 25, 2011 (JP) ................................ 2011-068659

(51) Int. Cl.
*G01T 1/20* (2006.01)
(52) U.S. Cl.
USPC ........................................................ 250/362
(58) Field of Classification Search
USPC ........................................................ 250/362
See application file for complete search history.

(56) References Cited

U.S. PATENT DOCUMENTS

| 7,442,937 B2 * | 10/2008 | Tsuchiya et al. ............ 250/363.1 |
| 7,768,002 B2 | 8/2010 | Kitamura et al. |
| 7,847,258 B2 | 12/2010 | Yaegashi et al. |

FOREIGN PATENT DOCUMENTS

| JP | 2001212119 A | 8/2001 |
| JP | 2003038483 A | 2/2003 |
| JP | 2003260053 A | 9/2003 |
| JP | 4217443 B2 | 11/2008 |
| JP | 4217506 B2 | 11/2008 |
| JP | 2009-032854 A | 2/2009 |
| JP | 2009-212389 A | 9/2009 |
| JP | 2009-219538 A | 10/2009 |
| JP | 4500400 B2 | 4/2010 |

OTHER PUBLICATIONS

Machine translation of JP 2003-038483 (Fujii).*
Takeda et al., "Fourier-transform method of fringe-pattern analysis for computer-based topography and interferometry" J. Opt. Soc. Am. vol. 72, No. 1 (1982).*
Notice of Reasons for Rejection, dated Feb. 12, 2013, issued in corresponding JP Application No. 2011-068659, 4 pages in English and Japanese.

* cited by examiner

*Primary Examiner* — David Porta
*Assistant Examiner* — Edwin Gunberg
(74) *Attorney, Agent, or Firm* — Sughrue Mion, PLLC

(57) ABSTRACT

A radiographic image capturing system includes a radiographic image capturing device, a grid, an acquiring unit, and a processor. The radiographic image capturing device includes a radiation detector in which pixels having a sensitivity with respect to radiation or light are disposed two-dimensionally at a predetermined pixel spacing. The grid is placed on a radiation source side of the radiation detector, and includes radiation absorbing members that are disposed at a predetermined spacing. The acquiring unit acquires an inclination angle of the grid, with respect to an array direction of the pixels, with which a spatial frequency of moiré fringes generated by the absorbing members in a captured radiographic image will be equal to or greater than a predetermined spatial frequency. The processor executes predetermined processing for making a relative angle between the grid and the radiation detector the acquired inclination angle.

18 Claims, 23 Drawing Sheets

FIG. 6A
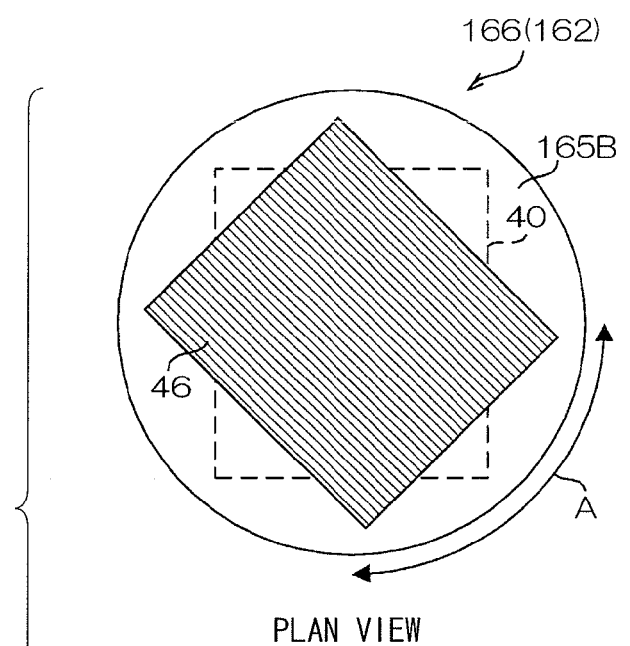
PLAN VIEW
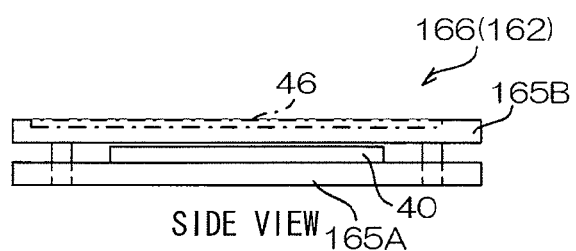
SIDE VIEW
FIG. 6B

FIG.14

INITIAL INFORMATION INPUT SCREEN

PLEASE INPUT NAME OF SUBJECT, IMAGING TARGET REGION, IMAGING POSTURE, EXPOSURE CONDITIONS, AND TYPES OF ELECTRONIC CASSETTE AND GRID TO BE USED.

NAME
IMAGING TARGET REGION
IMAGING POSTURE

IMAGING CONDITIONS
    TUBE VOLTAGE
    TUBE CURRENT
    DURATION OF EXPOSURE

TYPE OF ELECTRONIC CASSETTE
TYPE OF GRID

END

PLAN VIEW

SIDE VIEW
(STATE IN WHICH PINS ARE PUSHED OUT)

SIDE VIEW
(STATE IN WHICH PINS ARE PULLED IN)

IN CASE OF 60 LINES,
INCLINED AND NOT INCLINED

IN CASE OF 40 LINES,
sin θ = 0.25

IN CASE OF 40 LINES,
sin θ = 0.06

RADIOGRAPHIC IMAGE CAPTURING SYSTEM, PROGRAM STORAGE MEDIUM, AND METHOD

CROSS-REFERENCE TO RELATED APPLICATION

This application claims priority under 35 USC 119 from Japanese Patent Application No. 2011-068659 filed on Mar. 25, 2011, the disclosure of which is incorporated by reference herein.

BACKGROUND OF THE INVENTION

1. Field of the Invention

The present invention pertains to a radiographic image capturing system, a program storage medium, and a method, and particularly relates to a radiographic image capturing system that captures radiographic images using a grid for removing scatter radiation caused by a subject, a storage medium in which is stored a program that is executed in the radiographic image capturing system, and a method.

2. Description of the Related Art

In recent years, radiation detectors such as flat panel detectors (FPD), in which a radiation-sensitive layer is placed on a thin-film transistor (TFT) active matrix substrate and which can convert radiation directly into digital data, have been put into practical use. Radiographic image capturing devices that use these radiation detectors to capture radiographic images expressed by applied radiation have also been put into practical use. Types of radiation detectors used in these radiographic image capturing devices include indirect conversion radiation detectors, which convert radiation into light by means of a scintillator and thereafter convert the light into an electric charge by means of a semiconductor layer such as a photodiode, and direct conversion radiation detectors, which convert radiation into an electric charge by means of a semiconductor layer such as amorphous selenium. In each type, there exist various materials that can be used for the semiconductor layer.

In this type of radiographic image capturing device, a grid in which a material whose radiation absorption rate is high and a material whose radiation absorption rate is low are arranged side by side parallel to each other and alternating at regular intervals is used to remove scatter radiation scattered by the subject. There have been cases where, due to the difference between the spatial frequency (the spacing, with respect to the array direction, of the material whose radiation absorption rate is high) that the grid has and the spatial sampling period (detection pixel spacing) of the radiation detector, moiré fringes arise in the image obtained by the radiation detector.

That is, the Nyquist frequency $f_N$ [lines/cm] of a radiation detector with a pixel spacing $\Delta$ [cm] is expressed by the following expression (1).

$$f_N = \frac{1}{2 \times \Delta} \quad (1)$$

For example, if the pixel spacing $\Delta$ is 150 [μm], the Nyquist frequency is 33.3 [lines/cm]. Further, in a grid in which the number of lines, per 1 cm in the array direction, of the material whose radiation absorption rate is high (hereinafter called "the radiation absorbing material") is $f_G$ [lines/cm], the number of lines $f_G'$ [lines/cm] per 1 cm of the radiation absorbing material in the radiographic image is expressed by the following expression (2), and moiré fringes are generated in the spatial frequency (hereinafter also simply called "frequency") of $f_G'$ in a case in which the grid has been placed with respect to a radiation detector in such a way as to align the array direction of the radiation absorbing material with the pixel array direction of the radiation detector.

$$f_G' = \min(f_G - 2N_G f_N, 2(N_G+1)f_N - f_G) \quad (2)$$

$N_G$ in expression (2) is an integer equal to or greater than 0 (zero) and is expressed by the following expression (3). Here, the brackets in expression (3) are symbols meaning the decimal point and all numbers thereafter are discarded.

$$N_G = \left[ \frac{f_G}{2 \times f_N} \right] \quad (3)$$

As a technology that can be applied for preventing the generation of moiré fringes, Japanese Patent No. 4,500,400 discloses an image acquiring device that acquires an image by two-dimensionally sampling X-rays that have passed through a subject. The image acquiring device is equipped with an image acquiring unit that acquires an image by two-dimensionally sampling X-rays, a scatter radiation removing grid that is placed between the image acquiring unit and the subject and has a spacing that is from 30% to 40% of a sampling frequency sampled by the image acquiring unit, an image processing unit that removes grid lines caused by the scatter radiation removing grid, and a selection unit that automatically selects whether or not to remove the grid lines with the image processing unit based on information on an imaging site.

Expression (2) may appear complicated, but as shown in FIG. 20, it simply means that the spatial frequency $f_G'$ takes values that draw a line that is reflected (folded) at the vertical lines of the Nyquist frequency $f_N$ and $f=0$, which are serving as walls.

For example, $N_G$ with respect to a grid in which the number of lines $f_G$ is 60 [lines/cm] is 0 (zero), and $f_G'$ is 6.66 [lines/cm] as shown in the following expression (4).

$$f_G' = \min(f_G, 2f_N - f_G) = \min(60, 2 \times 33.33 - 60) = \min(60, 6.66) = 6.66 \quad (4)$$

An upper limit value $f_\mu$ of the spatial frequency of human body signals obtained by Fourier transforming, and mapping in a frequency space, image information (data) representing a radiographic image expressed by radiation that has passed through a human body is usually a low frequency and, although it depends on the site being imaged, it is estimated that there is virtually no information in signals in a frequency band of 20 [lines/cm] or greater. Supposing that μ (e.g., μ=0.6) represents the ratio of this upper limit value $f_\mu$ with respect to the Nyquist frequency $f_N$, when it satisfies the following expression (6), human body signals are not impaired much even if signals of a frequency around $f_G'$ are removed by image processing.

$$f_G' > \mu f_N = f_\mu \quad (0 < \mu < 1) \quad (5)$$

that is, $$(2N_G + 1 - \mu)f_N \leq f_G \leq (2N_G + 1 + \mu)f_N \quad (6)$$

As shown in FIG. 20 as an example, usually a direct conversion radiation detector has a sensitivity in a frequency across 200 [lines/cm] or more, and in an indirect conversion radiation detector, the scintillator has a sensitivity up to about $f_0 \approx 80$ [lines/cm] (i.e., the signal strength is greater than 0 (zero) in a frequency up to about $f_0 \approx 80$ [lines/cm]). For that reason, it is necessary for a direct conversion radiation detector to always satisfy expression (5), and for an indirect conversion radiation detector, necessary that the harmonic expressed by the following expression (e.g., in the case of $N=2$, $f_{2G}'$ obtained by solving $f_G$ as $f_{2G}=2f_G$ in expression (2)) satisfies expression (5).

$$Nf_G < f_0 (N > 1)$$

In an indirect conversion radiation detector, if a grid with a relatively large number of lines (e.g., $f_G \approx 2f_N$) is chosen, the harmonic can be made into a high frequency with no sensitivity, but the folding frequency $f_G'$ will position in a low frequency ($f_G' \approx 0 < \mu f_N$) that cannot be ignored. If a grid with a relatively small number of lines (e.g., $f_G \approx f_N$) is chosen, the folding frequency $f_G'$ will be a high frequency, but the harmonic $f_{2G}'$ comes in a frequency band to which the scintillator has a sensitivity, so the folding frequency $f_{2G}'$ will position in a low frequency ($f_{2G}' \approx 0 < \mu f_N$) that cannot be ignored.

With respect to this, there is also a technique that chooses a grid or a pixel spacing in which the harmonic satisfies $Nf_G' > f_\mu'$ as described in Japanese Patent No. 4,500,400, but adopting this technique restricts the design of the pixel spacing and so forth.

SUMMARY

In consideration of the above, the present invention provides a radiographic image capturing system, a program storage medium, and a method that can easily prevent the generation of moiré fringes without limiting the configuration of a grid or a radiation detector.

First, the principle of the present invention will be described.

The present invention minimizes side effects on a radiographic image by shifting moiré fringes caused by a grid, including harmonics, to the high frequency area (making moiré fringes into a frequency that has no effect on the detection of human body signals).

As shown in FIG. 20 as an example, a direct conversion radiation detector forms a latent image using an electric field (acquires a latent image directly by an electric charge), so signals are obtained up to a frequency of about 200 [lines/cm], but an indirect conversion radiation detector first converts radiation into light and then converts the light into an electric charge, and since this light blurs, signals are obtained only up to a frequency of about 80 [lines/cm].

The present invention, as shown in FIG. 21 and FIG. 22 as an example, utilizes the fact that the folding of signals in a diagonal direction becomes more complex in a two-dimensional frequency space than in a one-dimensional frequency space.

Here, a spatial frequency in a diagonal direction folds its line in the diagonal direction at a rectangular boundary enclosed by the Nyquist frequency $f_N$ of the vertical axis and the horizontal axis. When a grid is disposed diagonally inclined by angle $\theta$ from the direction of the vertical lines, the number of lines in the horizontal direction is $f_G \cos \theta$, and the frequency in the vertical direction is $f_G \sin \theta$. When this frequency folds, the horizontal and vertical spatial frequencies $f_{GX}'$ and $f_{GY}'$ of moiré fringes on the image are respectively expressed by the following expression (7) and expression (8).

$$f_{GX}'=\min(f_G \cos \theta - 2N_x f_N, 2(N_x+1)f_N - f_G \cos \theta)(N_x = [f_G \cos \theta/(2f_N)]) \quad (7)$$

$$f_{GY}'=\min(f_G \sin \theta - 2N_y f_N, 2(N_y+1)f_N - f_G \sin \theta)(N_Y = [f_G \sin \theta/(2f_N)]) \quad (8)$$

As shown in expression (7) and expression (8), in this case, $\sin \theta$ and $\cos \theta$ are each simply added with respect to expression (2) in the case of a one-dimensional frequency space.

Here, $f_G'$ is expressed by the following expression, and the angle $\theta$ is calculated from the pixel spacing of the radiation detector and the number of lines [lines/cm] of the grid in such a way as to satisfy $f_G' > \mu f_N$.

$$f_G' = \sqrt{f_{GX}'^2 + f_{GY}'^2}$$

These expressions are the same even with harmonics ($2 \times f_G, 3 \times f_G, \ldots$), and the range of the angle $\theta$ that satisfies the above condition differs per harmonic N.

Further, the optimum $\mu$ expressing human body signals differs per imaging site. For example, in the case of a grid in which $f_N = 33.3$ [lines/cm], $\mu$ is about 0.4 in the chest where there are many soft structures (low frequencies), and $\mu$ is about 0.6 in orthopedics where there are many bone trabeculae (high frequencies). Because $\mu$ differs per imaging site in this way, the range of the angle $\theta$ obtained by the above calculations also differs per imaging site. A case where $\mu$ is 0.6 will be described as an example below, but the same holds true also regarding cases other than where $\mu$ is 0.6.

In the case of a grid with 60 [lines/cm], as shown in FIG. 25, when the grid is disposed without being inclined with respect to the array direction of the pixels of the radiation detector, the frequency of moiré fringes on the radiographic image is 6.66 [lines/cm], in which human body signals cannot be distinguished from the low frequency pattern, and removal is difficult. However, in a case in which the grid is disposed inclined by 45 degrees, the frequency of moiré fringes on the radiographic image is $f_{GX}'=f_{GY}'=24.2$ [lines/cm], that is $f_G'=34.3$ [lines/cm], which satisfies $f_G' > \mu f_N = 20$ [lines/cm]. The second harmonic can be likewise calculated as a case of the grid with 120 [lines/cm], but it does not appear in the image because the high frequency signal strength of the scintillator is substantially 0 (zero).

In the case of a grid with 40 [lines/cm], if the angle $\theta=0$, moiré fringes in the second harmonic of 80 [lines/cm] are unable to be removed because they are imaged in a frequency of 13.33 [lines/cm], but if the angle $\theta$ satisfies the following condition, it results in fringes in a removable range, including those in the second harmonic of 80 [lines/cm]. (For example, $\theta=45$ degrees is not included in the range of expression (9) because $\sin \theta=0.707$.)

$$0.25 < \sin \theta < 0.6 \quad (9)$$

As shown in FIG. 23, by ensuring that the locus of the folding touches a circle with a radius $\mu f_N$ whose center is an origin point, harmonics of moiré fringes are not included inside the circle, so even up to the third harmonic in a case in which a grid in which the number of lines is small has been used, moiré fringes can be shifted to the high frequency side. Here, "touches a circle with a radius $\mu f_N$" is a case in which the grid is inclined by the angle $\theta$ that satisfies the following expression (10).

$$\sin \theta = \frac{\mu}{2} \quad (10)$$

However, because $\mu < 1$, the angle $\theta$ in expression (10) is smaller than 30 degrees. As shown in FIG. 24, in the case of $\mu=0.6$, $\theta=17.45$ degrees, and, for example, in the case of a grid in which the pixel spacing of the radiation detector is 150 μm and $f_N / \cos \theta = 35$ [lines/cm], moiré fringes can be shifted to the high frequency side in up to the fifth harmonic.

FIG. 25 exemplifies a two-dimensional frequency space in a case in which a grid with 60 [lines/cm] is disposed inclined by 45 degrees and a case in which the grid is not inclined. FIG. 26 exemplifies a two-dimensional frequency space in a case in which a grid with 40 [lines/cm] is disposed inclined by sin θ=0.25. FIG. 27 exemplifies a two-dimensional frequency space in a case in which a grid with 40 [lines/cm] is disposed inclined by sin θ=0.6.

The description that has been given up to here holds true even if the vertical axis and the horizontal axis are reversed. In this case, it suffices to replace sin θ with cos θ in expression (9) and expression (10), and the angle θ that touches the circle will be larger than 60 degrees.

By making the relative angle between the radiation detector and the grid the angle θ, moiré fringes can be shifted further to the high frequency side than human body signals. As a result, the frequency bands of human body signals and those of moiré fringes can be made different. However, since moiré fringes are generated in the high frequency band of the radiographic image, it is necessary to remove those moiré fringes. The spatial frequency which is the target of removal of the moiré fringes can be easily determined by Fourier transforming the radiographic image and searching for the peak value (maximum value). At this time, as long as the spatial frequency that is the target of removal is identified on the two-dimensional frequency space, a two-dimensional band-stop filter that stops the passage of that component can be easily created. In this case, although a two-dimensional high-pass filter may be used, in order to minimize side effects caused by filtering, using a band-stop filter whose frequency band is restricted much as possible is preferred.

Supposing that pixel spacing is fixed for a radiation detector, and that μ is held as a fixed value decided based on an image quality evaluation or the like, the range of the angle θ can be determined in accordance with the number of lines of the grid that is to be used.

In the above description, a case has been described in which the frequency bands of human body signals and moiré fringes are made different by shifting the frequency bands of moiré fringes further to the high frequency side than those of human body signals. However, it is not necessary to invariably shift all moiré fringes further to the high frequency side than those of human body signals. The effect on human body signals in a case in which moiré fringes have been removed can be alleviated by shifting the spatial frequency band of the moiré fringes in a direction away from the center position of the spatial frequency band of the human body signals.

On the basis of the above principle, a first aspect of the present invention is A radiographic image capturing system including: a radiographic image capturing device that includes a radiation detector in which pixels having a sensitivity with respect to radiation or light into which radiation has been converted are disposed two-dimensionally at a predetermined pixel spacing, and that captures a radiographic image expressed by radiation applied to an imaging surface; a grid that is placed on a radiation source side of the radiation detector, the grid including absorbing members that are disposed at a predetermined spacing and absorb radiation; an acquiring unit that acquires an angle of inclination of the grid, with respect to an array direction of the pixels of the radiation detector, with which a spatial frequency of moiré fringes generated by the absorbing members of the grid in the radiographic image captured by the radiation detector is equal to or greater than a predetermined spatial frequency; and a processor that executes predetermined processing for making a relative angle between the grid and the radiation detector the acquired angle of inclination.

According to this aspect, the generation of moiré fringes can be prevented easily without limiting the configuration of the grid or the radiation detector.

In the first aspect, the predetermined spatial frequency may be a spatial frequency of human body signals obtained by Fourier transforming, and mapping in a frequency space, a radiographic image representing a human body.

Thereby, the generation of moiré fringes can be prevented more reliably.

In the first aspect, the spatial frequency of the human body signals may be predetermined per site, which is into an imaging target by the radiographic image capturing device.

Thereby, the generation of moiré fringes can be prevented more reliably.

In the first aspect, the acquiring unit may acquire the angle of inclination by using a spatial frequency $f_G'$ obtained by the following expression and a ratio μ of an upper limit value $f_\mu$ of the spatial frequency of the human body signals with respect to the Nyquist frequency $f_N$ to calculate an angle θ that satisfies $f_G' > \mu f_N$:

$$f_{GX}' = \min(f_G \cos\theta - 2N_X f_N, 2(N_X+1)f_N - f_G \cos\theta)(N_X = [f_G \cos\theta/(2f_N)])$$

$$f_{GY}' = \min(f_G \sin\theta - 2N_Y f_N, 2(N_Y+1)f_N - f_G \sin\theta)(N_Y = [f_G \sin\theta/(2f_N)])$$

$$f_G' = \sqrt{f_{GX}'^2 + f_{GY}'^2} \quad \text{[Expression]}$$

where $f_G$ is the number of lines, per 1 cm with respect to the array direction, of the absorbing members disposed in the grid, $f_N$ is the Nyquist frequency [lines/cm] defined by the pixel spacing of the radiation detector, and θ is the relative angle [degrees] between the grid and the radiation detector.

In the first aspect, the radiographic image capturing system may further include a changing unit that changes a relative angle between the radiographic image capturing device and the grid, wherein the processor executes, as the predetermined processing, processing that controls the changing unit in such a way that the relative angle becomes the acquired angle of inclination.

Thereby, convenience can be improved more in radiographic image capturing compared to a case in which the relative angle between the radiographic image capturing device and the grid is set manually.

In the first aspect, the processor may execute, as the predetermined processing, processing that provides notification of the acquired angle of inclination.

Thereby, the angle of inclination can be grasped easily.

In the first aspect, the radiographic image capturing system may further include an identifying unit that identifies a spatial frequency of moiré fringes generated by the absorbing members in the radiographic image; and an image processing unit that performs image processing that removes, from the radiographic image, a component of the identified spatial frequency.

Thereby, the generation of moiré fringes can be prevented more reliably.

A second aspect of the present invention is a radiographic image capturing system including: a radiographic image capturing device that includes a radiation detector in which pixels having a sensitivity with respect to radiation or light into which radiation has been converted are disposed two-dimensionally at a predetermined pixel spacing, and that captures an image expressed by radiation applied to an imaging surface;

an acquiring unit that acquires a type of a grid that is placed on a radiation source side of the radiation detector, and that includes absorbing members which are disposed at a predetermined spacing and absorb radiation, and an angle of inclination of the grid, with respect to an array direction of the pixels of the radiation detector, that can make a spatial frequency of moiré fringes generated by the absorbing members of the grid in the radiographic image captured by the radiation detector equal to or greater than a predetermined spatial frequency; and a notifying unit that provides notification of the type and the angle of inclination of the grid acquired by the acquiring unit.

According to the second aspect, the generation of moiré fringes can be prevented easily without limiting the configuration of the grid or the radiation detector.

In the second aspect, the acquiring unit may acquire the type and the angle of inclination of the grid per site, which is an imaging target by the radiographic image capturing device.

Thereby, the generation of moiré fringes can be prevented more reliably.

A third aspect of the present invention is a non-transitory storage medium that stores a program that executes processing in a radiographic image capturing system including a radiographic image capturing device that has a radiation detector in which pixels having a sensitivity with respect to radiation or light into which radiation has been converted are disposed two-dimensionally at a predetermined pixel spacing, and that captures a radiographic image expressed by radiation applied to an imaging surface, and a grid that is placed on a radiation source side of the radiation detector, the grid including absorbing members that are disposed at a predetermined spacing and absorb radiation, the processing including: acquiring an angle of inclination of the grid, with respect to an array direction of the pixels of the radiation detector, with which a spatial frequency of moiré fringes generated by the absorbing members of the grid in the radiographic image captured by the radiation detector is equal to or greater than a predetermined spatial frequency; and executing predetermined processing for making a relative angle between the grid and the radiation detector the acquired angle of inclination.

A fourth aspect of the present invention is a method of operating a radiographic image capturing system including a radiographic image capturing device that has a radiation detector in which pixels having a sensitivity with respect to radiation or light into which radiation has been converted are disposed two-dimensionally at a predetermined pixel spacing, and that captures a radiographic image expressed by radiation applied to an imaging surface, and a grid that is placed on a radiation source side of the radiation detector, the grid including absorbing members that are disposed at a predetermined spacing and absorb radiation, the method including: acquiring an angle of inclination of the grid, with respect to an array direction of the pixels of the radiation detector, with which a spatial frequency of moiré fringes generated by the absorbing members of the grid in the radiographic image captured by the radiation detector is equal to or greater than a predetermined spatial frequency; and executing predetermined processing for making a relative angle between the grid and the radiation detector the acquired angle of inclination.

According to the third and fourth aspects, the generation of moiré fringes can be prevented easily without limiting the configuration of the grid or the radiation detector.

BRIEF DESCRIPTION OF THE DRAWINGS

An exemplary embodiment of the present invention will be described in detail based on the following figures, wherein:

FIG. 6A is a plan view showing the configuration of a holding unit pertaining to the exemplary embodiment, and FIG. 6B is a side view showing the configuration of the holding unit;

FIG. 14 is a schematic diagram showing an example of an initial information input screen pertaining to the exemplary embodiment;

DETAILED DESCRIPTION

An exemplary embodiment of the present invention will be described in detail below with reference to the drawings. Here, an example of a case in which the present invention is applied to a radiology information system, which is a system that as a whole manages information handled in a radiology department in a hospital, will be described.

Figure 1:
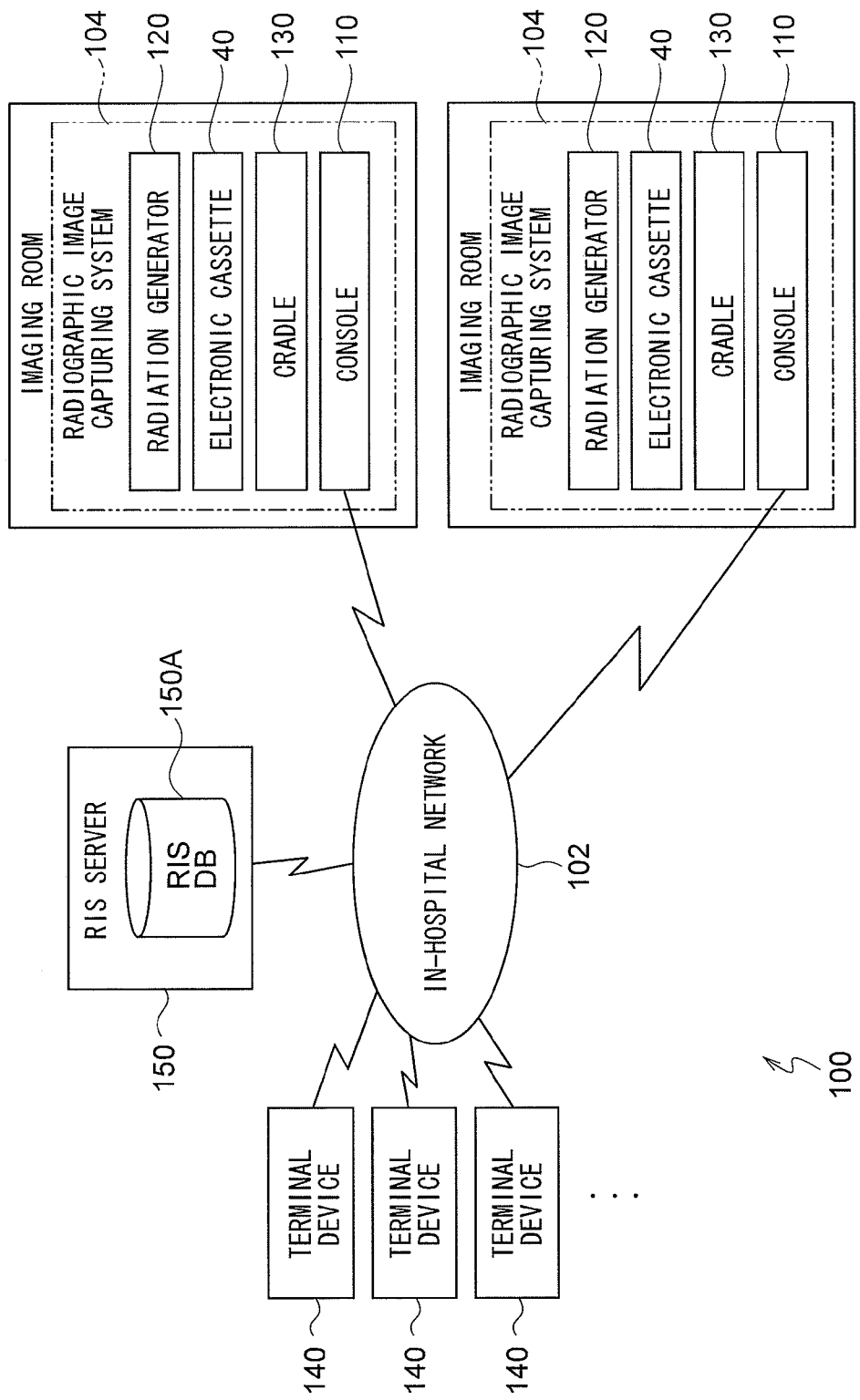
FIG. 1 is a block diagram showing the configuration of a radiology information system pertaining to the exemplary embodiment.

First, the configuration of a radiology information system (RIS) 100 (hereinafter called "the RIS 100") pertaining to the present exemplary embodiment will be described with reference to FIG. 1.

The RIS 100 is a system for managing information such as medical service appointments and diagnostic records in a radiology department and configures part of a hospital information system (hereinafter called "the HIS").

The RIS 100 has plural imaging request terminal devices 140 (hereinafter called "the terminal device(s) 140"), an RIS server 150, and radiographic image capturing systems 104 (hereinafter called "the imaging system(s) 104"). The imaging systems 104 are installed in individual radiographic imaging rooms (or operating rooms) in a hospital. The RIS 100 is configured as a result of the terminal devices 140, the RIS server 150, and the imaging systems 104 being connected to an in-hospital network 102 configured by a wired or wireless local area network (LAN). The RIS 100 configures part of the HIS disposed in the same hospital, and an HIS server (not shown in the drawings) that manages the entire HIS is also connected to the in-hospital network 102.

The terminal devices 140 are for doctors or radiologic technologists to input and browse diagnostic information and facility reservations. Radiographic imaging requests and imaging reservations are also made via the terminal devices 140. Each of the terminal devices 140 is configured to include a personal computer having a display device, and the terminal devices 140 are made capable of intercommunicating with the RIS server 150 via the in-hospital network 102.

The RIS server 150 receives the imaging requests from each of the terminal devices 140 and manages radiographic imaging schedules in the imaging systems 104. The RIS server 150 includes a database 150A.

The database 150A includes: information relating to patients (subjects), such as attribute information (names, sexes, dates of birth, ages, blood types, body weights, patient identifications (IDs), etc.), medical histories, consultation histories, radiographic images that have been captured in the past, etc.; information relating to later-described electronic cassettes 40 used in the imaging systems 104, such as identification numbers (ID information), models, sizes, sensitivities, dates of first use, numbers of times used, etc.; and environment information representing the environments in which radiographic images are captured using the electronic cassettes 40—that is, the environments in which the electronic cassettes 40 are used (e.g., radiographic imaging rooms, operating rooms, etc.).

The imaging systems 104 capture radiographic images as a result of being operated by the doctors or the radiologic technologists in response to an instruction from the RIS server 150. Each of the imaging systems 104 is equipped with a radiation generator 120, an electronic cassette 40, a cradle 130, and a console 110. The radiation generator 120 applies a dose of radiation X (see also FIG. 7) according to exposure conditions from a radiation source 121 (see also FIG. 2) to a subject. The electronic cassette 40 has a built-in radiation detector 20 (see also FIG. 7) that absorbs the radiation X that has passed through an imaging target site of the subject, generates electric charges, and creates image information representing a radiographic image on the basis of the generated electric charge quantity. The cradle 130 charges a battery that is built into the electronic cassette 40. The console 110 controls the electronic cassette 40 and the radiation generator 120.

The console 110 acquires various types of information (data) stored in the database 150A from the RIS server 150, stores the data in a later-described HDD 116 (see FIG. 9), uses the data as needed to control the electronic cassette 40 and the radiation generator 120.

Figure 2:
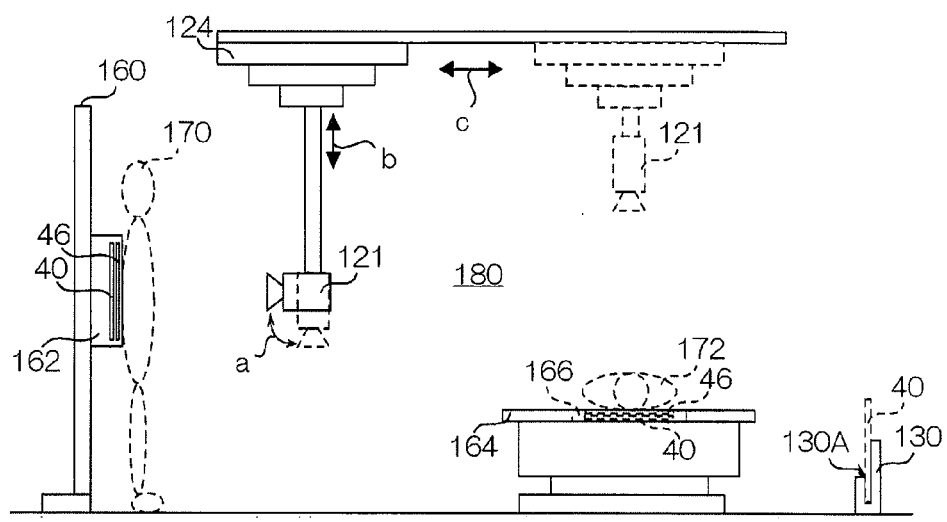
FIG. 2 is a side view showing an example arrangement of devices, in a radiographic imaging room, of a radiographic image capturing system pertaining to the exemplary embodiment.

FIG. 2 shows an example arrangement of the devices, in a radiographic imaging room 180, of the imaging system 104 pertaining to the present exemplary embodiment.

As shown in FIG. 2, a standing position stand 160, which is used when performing radiographic imaging in a standing position, and a lying position table 164, which is used when performing radiographic imaging in a lying position, are installed in the radiographic imaging room 180. The space in front of the standing position stand 160 serves as a subject imaging position 170 when performing radiographic imaging in the standing position. The space above the lying position table 164 serves as a subject imaging position 172 when performing radiographic imaging in the lying position.

A holding unit 162 that holds the electronic cassette 40 and a grid 46 is disposed in the standing position stand 160. The electronic cassette 40 and the grid 46 are held in the holding unit 162 when capturing a radiographic image in the standing position. Similarly, a holding unit 166 that holds the electronic cassette 40 and the grid 46 is disposed in the lying position table 164. The electronic cassette 40 and the grid 46 are held in the holding unit 166 when capturing a radiographic image in the lying position.

The grid 46 is for removing scatter radiation that has been scattered by the subject. The grid 46 is configured by a material whose radiation absorption rate is high (in the present exemplary embodiment, lead) and a material whose radiation absorption rate is low (in the present exemplary embodiment, air) being arranged side by side parallel to each other and alternating at regular intervals.

Further, a supporting and moving mechanism 124 is disposed in the radiographic imaging room 180. In order to enable both radiographic imaging in the standing position and in the lying position by the radiation from the single radiation source 121, the supporting and moving mechanism 124 supports the radiation source 121 in such a way that the radiation source 121 is rotatable about a horizontal axis (the direction of arrow a in FIG. 2), is movable in the vertical direction (the direction of arrow b in FIG. 2), and is movable in the horizontal direction (the direction of arrow c in FIG. 2). The supporting and moving mechanism 124 includes a drive source that rotates the radiation source 121 about the horizontal axis, a drive source that moves the radiation source 121 in the vertical direction, and a drive source that moves the radiation source 121 in the horizontal direction (none of the drive sources are shown in the drawings).

An accommodating portion 130A that can accommodate the electronic cassette 40 is formed in the cradle 130.

When the electronic cassette 40 is not in use, the electronic cassette 40 is accommodated in the accommodating portion 130A of the cradle 130, and the built-in battery of the electronic cassette 40 is charged by the cradle 130. When a radiographic image is to be captured, the electronic cassette 40 is removed from the cradle 130 by, for example, a radiologic technologist and is held in the holding unit 162 of the standing position stand 160 if the imaging posture is the standing position or is held in the holding unit 166 of the lying position table 164 if the imaging posture is the lying position.

In the imaging system 104 pertaining to the present exemplary embodiment, various types of information (data) are transmitted and received by wireless communication between the radiation generator 120 and the console 110 and between the electronic cassette 40 and the console 110.

Figure 3:
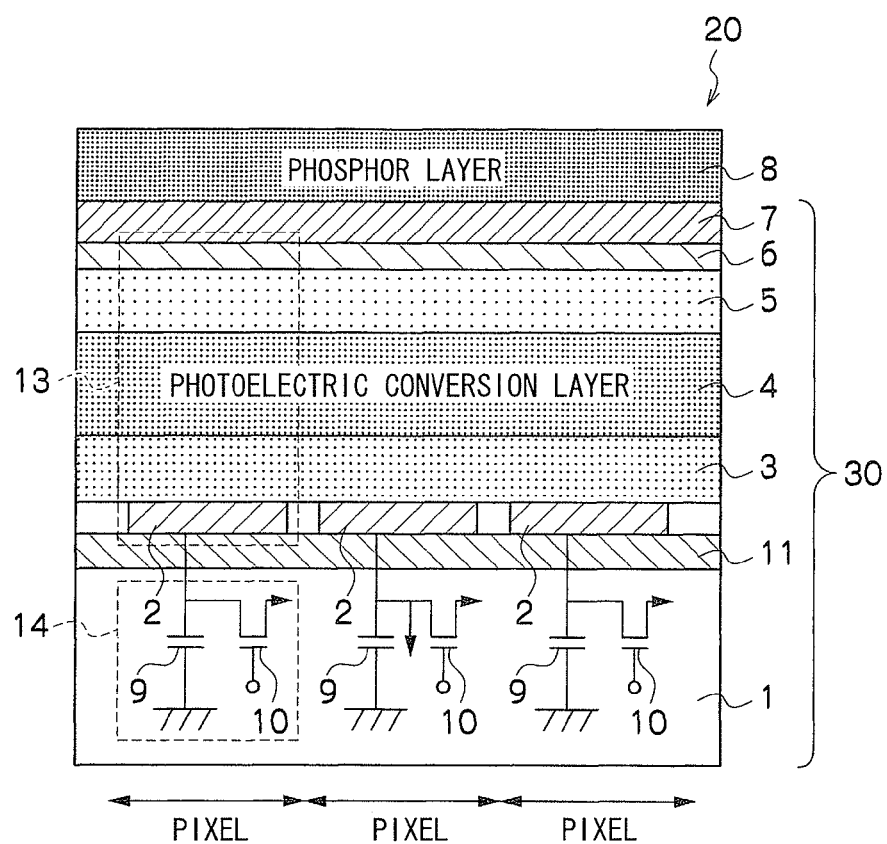
FIG. 3 is a cross-sectional schematic view showing the schematic configuration of a portion including three pixels of a radiation detector pertaining to the exemplary embodiment.

Next, the configuration of the radiation detector 20 pertaining to the present exemplary embodiment will be described. FIG. 3 is a cross-sectional schematic diagram schematically showing a portion including three pixels of the radiation detector 20 pertaining to the present exemplary embodiment.

As shown in FIG. 3, in the radiation detector 20 pertaining to the present exemplary embodiment, signal output portions 14, sensor portions 13, and a scintillator 8 are sequentially layered on an insulating substrate 1. Pixels are configured by the signal output portions 14 and the sensor portions 13. The pixels are plurally arrayed on the substrate 1 and are configured in such a way that the signal output portion 14 and the sensor portion 13 in each pixel have overlap.

The scintillator 8 is formed on the sensor portions 13 with a transparent insulating film 7 being interposed therebetween. The scintillator 8 is formed of a phosphor material that converts radiation made incident thereon from above (the opposite side of the substrate 1) or below into light and emits light. By disposing the scintillator 8, the radiation that has passed through the subject is absorbed by the scintillator 8 and light is emitted.

It is preferred that the wavelength range of the light emitted by the scintillator 8 be in the visible light range (a wavelength of 360 nm to 830 nm). It is more preferred that the wavelength range of the light that the scintillator 8 emits include the green wavelength range in order to enable monochrome imaging by the radiation detector 20.

As the phosphor used for the scintillator 8, specifically a phosphor including cesium iodide (CsI) is preferred in the case of imaging using X-rays as the radiation. Using CsI(T1) (cesium iodide to which thallium has been added) whose emission spectrum when X-rays are applied is 420 nm to 700 nm is particularly preferred. The emission peak wavelength in the visible light range of CsI(T1) is 565 nm.

The sensor portions 13 have an upper electrode 6, lower electrodes 2, and a photoelectric conversion layer 4 that is placed between the upper electrode 6 and the lower electrodes 2. The photoelectric conversion layer 4 is configured by an organic photoelectric conversion material that absorbs the light emitted by the scintillator 8 and generates an electric charge.

It is preferred that the upper electrode 6 be configured by a conducting material that is transparent at least with respect to the emission wavelength of the scintillator 8 because it is necessary to allow the light produced by the scintillator 8 to be made incident on the photoelectric conversion layer 4. Specifically, using a transparent conducting oxide (TCO) whose transmittance with respect to visible light is high and whose resistance value is small is preferred. A metal thin film of Au or the like can also be used as the upper electrode 6, but its resistance value easily increases when trying to obtain a transmittance of 90% or more, so TCO is more preferred. For example, ITO, IZO, AZO, FTO, $SnO_2$, $TiO_2$, $ZnO_2$, etc. can be preferably used. ITO is most preferred from the standpoints of process ease, low resistance, and transparency. The upper electrode 6 may have a single configuration common to all the pixels or may be divided per pixel.

The photoelectric conversion layer 4 includes an organic photoelectric conversion material, absorbs the light emitted from the scintillator 8, and generates an electric charge corresponding to the absorbed light. The photoelectric conversion layer 4 including the organic photoelectric conversion material in this way has a sharp absorption spectrum in the visible range, virtually no electromagnetic waves other than the light emitted by the scintillator 8 are absorbed by the photoelectric conversion layer 4, and noise that is generated as a result of radiation such as X-rays being absorbed by the photoelectric conversion layer 4 can be effectively suppressed.

It is preferred that the absorption peak wavelength of the organic photoelectric conversion material configuring the photoelectric conversion layer 4 be as close as possible to the emission peak wavelength of the scintillator 8 so that the organic photoelectric conversion material most efficiently absorbs the light emitted by the scintillator 8. It is ideal that the absorption peak wavelength of the organic photoelectric conversion material and the emission peak wavelength of the scintillator 8 coincide, but as long as the difference between them is small, the organic photoelectric conversion material can sufficiently absorb the light emitted from the scintillator 8. Specifically, it is preferred that the difference between the absorption peak wavelength of the organic photoelectric conversion material and the emission peak wavelength of the scintillator 8 with respect to radiation be within 10 nm. It is more preferred that the difference be within 5 nm.

Examples of organic photoelectric conversion materials that can satisfy this condition include quinacridone organic compounds and phthalocyanine organic compounds. For example, the absorption peak wavelength in the visible range of quinacridone is 560 nm. Therefore, if quinacridone is used as the organic photoelectric conversion material and CsI(T1) is used as the material of the scintillator 8, it is possible to make the difference between the peak wavelengths within 5 nm and the amount of electric charge generated in the photoelectric conversion layer 4 can be substantially maximized.

Next, the photoelectric conversion layer 4 applicable to the radiation detector 20 pertaining to the present exemplary embodiment will be specifically described.

The electromagnetic wave absorption/photoelectric conversion material in the radiation detector 20 pertaining to the present exemplary embodiment can be configured by the pair of electrodes 2 and 6 and an organic layer that includes the photoelectric conversion layer 4 sandwiched between the electrodes 2 and 6. More specifically, the organic layer can be formed by stacking or mixing together a material that absorbs electromagnetic waves, a photoelectric conversion material, an electron-transporting material, a hole-transporting material, an electron-blocking material, a hole-blocking material, a crystallization preventing material, electrodes, an interlayer contact improving material, etc.

It is preferred that the organic layer contain an organic p-type compound or an organic n-type compound.

Organic p-type semiconductors (compounds) are donor organic semiconductors (compounds) represented mainly by hole-transporting organic compounds and refer to organic compounds having the property that they easily donate electrons. More specifically, organic p-type semiconductors (compounds) refer to organic compounds whose ionization potential is the smaller of the two when two organic materials are brought into contact with each other and used. Consequently, any organic compound can be used as the donor organic compound provided that it is an electron-donating organic compound.

Organic n-type semiconductors (compounds) are accepter organic semiconductors (compounds) represented mainly by electron-transporting organic compounds and refer to organic compounds having the property that they easily accept electrons. More specifically, organic n-type semiconductors (compounds) refer to organic compounds whose electron affinity is the greater of the two when two organic compounds are brought into contact with each other and used. Consequently, any organic compound can be used as the accepter organic compound provided that it is an electron-accepting organic compound.

Materials applicable as the organic p-type semiconductor and the organic n-type semiconductor, and the structure of the photoelectric conversion layer 4, are described in detail in JP-A No. 2009-32854, so descriptions thereof will be omitted here. The photoelectric conversion layer 4 may also be formed so as to further contain fullerenes or carbon nanotubes.

It is preferred that the thickness of the photoelectric conversion layer 4 be as large as possible in terms of absorbing the light from the scintillator 8. However, if the thickness of the photoelectric conversion layer 4 is thicker than a certain extent, the strength of the electric field generated in the photoelectric conversion layer 4 due to the bias voltage applied from both ends of the photoelectric conversion layer 4 drops and the electric charge become unable to be collected. For this reason, it is preferred that the thickness of the photoelectric conversion layer 4 be from 30 nm to 300 nm. It is more preferred that the film thickness of the photoelectric conversion layer 4 be from 50 nm to 250 nm. It is particularly preferred that the film thickness of the photoelectric conversion layer 4 be from 80 nm to 200 nm.

In the radiation detector 20 shown in FIG. 3, the photoelectric conversion layer 4 has a single configuration common to all the pixels, but the photoelectric conversion layer 4 may also be divided per pixel.

The lower electrodes 2 are thin films divided per pixel. The lower electrodes 2 can be configured by a transparent or opaque conducting material, and aluminum, silver, etc. can be suitably used.

The thickness of the lower electrodes 2 can be 30 nm to 300 nm, for example.

In the sensor portions 13, one of the electric charge (holes or electrons) generated in the photoelectric conversion layer 4 can be moved to the upper electrode 6 and the other can be moved to the lower electrodes 2 as a result of a predetermined bias voltage being applied between the upper electrode 6 and the lower electrodes 2. In the radiation detector 20, a wire is connected to the upper electrode 6, and the bias voltage is applied to the upper electrode 6 via this wire. The polarity of the bias voltage is decided in such a way that the electrons generated in the photoelectric conversion layer 4 move to the upper electrode 6 and the holes move to the lower electrodes 2, but this polarity may also be the opposite.

It suffices for the sensor portions 13 configuring each of the pixels to include at least the lower electrodes 2, the photoelectric conversion layer 4, and the upper electrode 6. However, in order to suppress an increase in dark current, disposing at least either of an electron-blocking film 3 and a hole-blocking film 5 is preferred, and disposing both is more preferred.

The electron-blocking film 3 can be disposed between the lower electrodes 2 and the photoelectric conversion layer 4. The electron-blocking film 3 can suppress electrons from being injected from the lower electrodes 2 into the photoelectric conversion layer 4 and dark current from increasing when the bias voltage has been applied between the lower electrodes 2 and the upper electrode 6.

Electron-donating organic materials can be used for the electron-blocking film 3.

It suffices for the material that is actually used for the electron-blocking film 3 to be selected in accordance with, for example, the material of the adjacent electrodes and the material of the adjacent photoelectric conversion layer 4. A material whose electron affinity (Ea) is greater by 1.3 eV or more than the work function (Wf) of the material of the adjacent electrodes and has an ionization potential (Ip) equal to or smaller than the ionization potential of the material of the adjacent photoelectric conversion layer 4 is preferred. Materials applicable as the electron-donating organic material are described in detail in JP-A No. 2009-32854, so descriptions thereof will be omitted here.

In order to allow the electron-blocking film 3 to reliably exhibit a dark current suppressing effect and to prevent a drop in the photoelectric conversion efficiency of the sensor portions 13, it is preferred that the thickness of the electron-blocking film 3 be from 10 nm to 200 nm. It is more preferred that the thickness of the electron-blocking film 3 be from 30 nm to 150 nm. It is particularly preferred that the thickness of the electron-blocking film 3 be from 50 nm to 100 nm.

The hole-blocking film 5 can be disposed between the photoelectric conversion layer 4 and the upper electrode 6. The hole-blocking film 5 can suppress holes from being injected from the upper electrode 6 into the photoelectric conversion layer 4 and dark current from increasing when the bias voltage has been applied between the lower electrodes 2 and the upper electrode 6.

Electron-accepting organic materials can be used for the hole-blocking film 5.

In order to allow the hole-blocking film 5 to reliably exhibit a dark current suppressing effect and to prevent a drop in the photoelectric conversion efficiency of the sensor portions 13, it is preferred that the thickness of hole-blocking film 5 be from 10 nm to 200 nm. It is more preferred that the thickness of the hole-blocking film 5 be from 30 nm to 150 nm. It is particularly preferred that the thickness of the hole-blocking film 5 be from 50 nm to 100 nm.

It suffices for the material that is actually used for the hole-blocking film 5 to be selected in accordance with, for example, the material of the adjacent electrode and the material of the adjacent photoelectric conversion layer 4. A material whose ionization potential (Ip) is greater by 1.3 eV or more than the work function (Wf) of the material of the adjacent electrode and has an electron affinity (Ea) equal to or greater than the electron affinity of the material of the adjacent photoelectric conversion layer 4 is preferred. Materials applicable as the electron-accepting organic material are described in detail in JP-A No. 2009-32854, so descriptions thereof will be omitted here.

In a case in which the bias voltage is set in such a way that, among the electric charge generated in the photoelectric conversion layer 4, the holes move to the upper electrode 6 and the electrons move to the lower electrode 2, the positions of the electron-blocking film 3 and the hole-blocking film 5 may be reversed. Further, the electron-blocking film 3 and the hole-blocking film 5 do not both have to be disposed; a certain degree of a dark current suppressing effect can be obtained as long as either is disposed.

Figure 4:
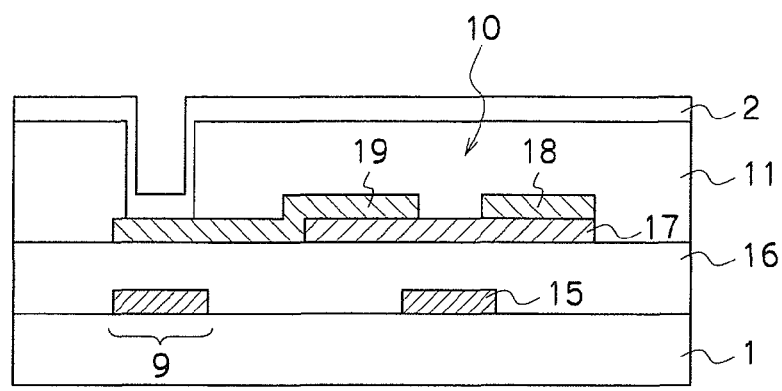
FIG. 4 is a cross-sectional side view schematically showing the configuration of a signal output portion of a portion including one pixel of the radiation detector pertaining to the exemplary embodiment.

The signal output portions 14 are formed on the surface of the substrate 1 below the lower electrodes 2 of each of the pixels. FIG. 4 schematically shows the configuration of the signal output portions 14.

As shown in FIG. 4, in each of the signal output portions 14, a capacitor 9 and a field-effect thin-film transistor (TFT) (hereinafter sometimes this will be simply called a "thin-film transistor") 10 are formed in correspondence to the lower electrode 2. The capacitor 9 stores the electric charge that has moved to the lower electrode 2. The thin-film transistor 10 converts the electric charge stored in the capacitor 9 into an electric signal and outputs the electric signal. The region in which the capacitor 9 and the thin-film transistor 10 are formed has a portion that overlaps the lower electrode 2 in a plan view. By forming the signal output portion 14 in this configuration, the signal output portion 14 and the sensor portion 13 in each of the pixels have an overlap in the thickness direction. In order to minimize the plane area of the radiation detector 20 (the pixels), it is preferred that the region in which the capacitor 9 and the thin-film transistor 10 are formed be completely covered by the lower electrode 2.

The capacitor 9 is electrically connected to the corresponding lower electrode 2 via a wire of a conductive material that is formed penetrating an insulating film 11 disposed between the substrate 1 and the lower electrode 2. Because of this, the electric charge trapped in the lower electrode 2 can be moved to the capacitor 9.

In the thin-film transistor 10, a gate electrode 15, a gate insulating film 16, and an active layer (channel layer) 17 are layered. Moreover, a source electrode 18 and a drain electrode 19 are formed a predetermined spacing apart from each other on the active layer 17.

The active layer 17 can, for example, be formed by amorphous silicon, an amorphous oxide, an organic semiconductor material, carbon nanotubes, etc. The material configuring the active layer 17 is not limited to these.

In a case in which the active layer 17 is configured by an amorphous oxide, oxides including at least one of In, Ga, and Zn (e.g., In—O amorphous oxides) are preferred, oxides including at least two of In, Ga, and Zn (e.g., In—Zn—O amorphous oxides, In—Ga—O amorphous oxides, or Ga—Zn—O amorphous oxides) are more preferred, and oxides including In, Ga, and Zn are particularly preferred. As an In—Ga—Zn—O amorphous oxide, an amorphous oxide whose composition in a crystalline state is expressed by $InGaO_3(ZnO)$, (where m is a natural number less than 6) is preferred, and particularly $InGaZnO_4$ is more preferred.

Examples of organic semiconductor materials capable of configuring the active layer 17 include phthalocyanine compounds, pentacene, and vanadyl phthalocyanine, but the organic semiconductor materials are not limited to these. Configurations of phthalocyanine compounds are described in detail in JP-A No. 2009-212389, so descriptions thereof will be omitted here.

By forming the active layer 17 of the thin-film transistor 10 from an amorphous oxide, an organic semiconductor material, or carbon nanotubes, the active layer 17 does not absorb radiation such as X-rays, or if it does absorb any radiation the radiation is an extremely minute amount, so the generation of noise in the signal output portion 14 can be effectively suppressed.

Further, in a case in which the active layer 17 is formed with carbon nanotubes, the switching speed of the thin-film transistor 10 can be increased, and the thin-film transistor 10 can be formed having a low degree of absorption of light in the visible light range. In the case of forming the active layer 17 with carbon nanotubes, the performance of the thin-film transistor 10 drops significantly simply by mixing an infinitesimal amount of a metal impurity into the active layer 17, so it is necessary to separate, extract, and form extremely high-purity carbon nanotubes using centrifugal separation or the like.

Here, the amorphous oxide, organic semiconductor material, or carbon nanotubes configuring the active layer 17 of the thin-film transistor 10 and the organic photoelectric conversion material configuring the photoelectric conversion layer 4 are all capable of being formed into films at a low temperature. Consequently, the substrate 1 is not limited to a substrate with high heat resistance, such as a semiconductor substrate, a quartz substrate, or a glass substrate, and a plastic or other flexible substrate, aramids, or bionanofibers can also be used. Specifically, polyester, such as polyethylene terephthalate, polybutylene phthalate, and polyethylene naphthalate, polystyrene, polycarbonate, polyethersulphone, polyarylate, polyimide, polycyclic olefin, norbornene resin, and poly (chloro-trifluoro-ethylene) or other flexible substrates can be used. By employing a flexible substrate made of plastic, the substrate can be made lightweight, which is advantageous for portability, for example.

Further, an insulating layer for ensuring insulation, a gas barrier layer for preventing the transmission of moisture and/or oxygen, an undercoat layer for improving flatness or adhesion to the electrodes or the like, or other layers may also be disposed on the substrate 1.

High-temperature processes of 200 degrees or higher can be applied to aramids, so a transparent electrode material can be hardened at a high temperature and given a low resistance, and aramids can also accommodate automatic packaging of driver ICs including solder reflow processes. Aramids also have a thermal expansion coefficient that is close to that of indium tin oxide (ITO) or a glass substrate, so they have little warping after manufacture and do not break easily. Further, aramids can also form a thinner substrate compared to a glass substrate or the like. An ultrathin glass substrate and an aramid may also be layered to form a substrate.

Further, bionanofibers are composites of cellulose microfibril bundles (bacterial cellulose) that a bacterium (Acetobacter xylinum) produces and a transparent resin. Cellulose microfibril bundles have a width of 50 nm, which is a size that is 1/10 with respect to visible wavelengths, and have high strength, high elasticity, and low thermal expansion. By impregnating and hardening a transparent resin such as an acrylic resin or an epoxy resin in bacterial cellulose, bionanofibers exhibiting a light transmittance of about 90% at a wavelength of 500 nm while including fibers at 60 to 70% can be obtained. Bionanofibers have a low thermal expansion coefficient (3 to 7 ppm) comparable to silicon crystal, a strength comparable to steel (460 MPa), high elasticity (30 GPa), and are flexible, so they enables to form a thinner substrate 1 compared to a glass substrate or the like.

In the present exemplary embodiment, a TFT substrate 30 is formed by sequentially forming the signal output portions 14, the sensor portions 13, and the transparent insulating film 7 on the substrate 1, and the radiation detector 20 is formed by adhering the scintillator 8 onto the TFT substrate 30 using, for example, an adhesive resin whose light absorbance is low.

Figure 5:
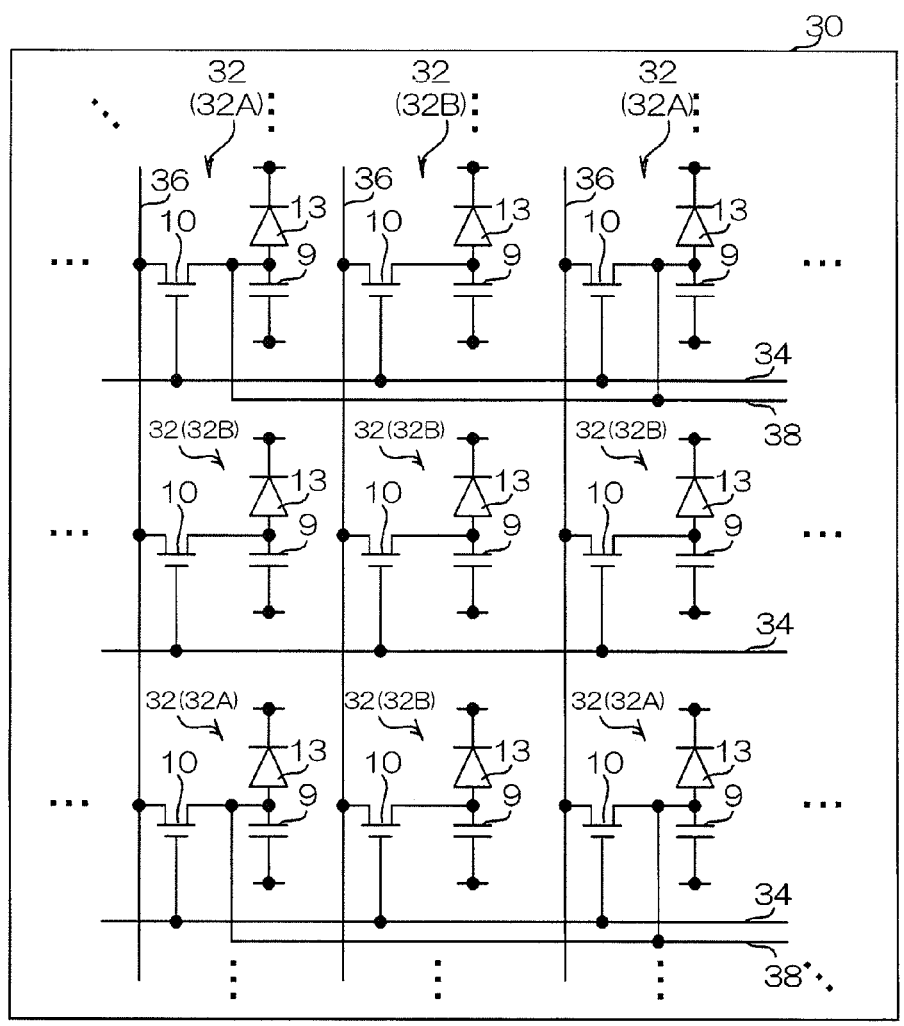
FIG. 5 is a plan view showing the configuration of the radiation detector pertaining to the exemplary embodiment.

As shown in FIG. 5, on the TFT substrate 30, pixels 32 including the sensor portions 13, the capacitors 9, and the thin-film transistors 10 are plurally disposed two-dimensionally in one direction (a row direction in FIG. 5) and an intersecting direction (a column direction in FIG. 5) with respect to the one direction.

Further, plural gate lines 34 that extends in the one direction (the row direction) and are for switching on and off the thin-film transistors 10 and plural data lines 36 that extends in the intersecting direction (the column direction) and are for reading out the electric charges via the thin-film transistors 10 in an on-state are disposed in the radiation detector 20.

The radiation detector 20 is formed in a tabular, quadrilateral shape having four sides on its outer edges in a plan view; more specifically, the radiation detector 20 is formed in a rectangular shape.

Here, in the radiation detector 20 pertaining to the present exemplary embodiment, some of the pixels 32 are used for detecting the state of application of the radiation, and the remaining pixels 32 capture radiographic images. Hereinafter, the pixels 32 for detecting the state of application of the radiation will be called radiation detecting pixels 32A, and the remaining pixels 32 will be called radiographic image acquiring pixels 32B.

The radiation detector 20 pertaining to the present exemplary embodiment cannot obtain pixel information (data) of radiographic images in the positions where the radiation detecting pixels 32A are placed because the radiation detector 20 captures radiographic images with the radiographic image acquiring pixels 32B excluding the radiation detecting pixels 32A of the pixels 32. For this reason, in the radiation detector 20, the radiation detecting pixels 32A are placed in such a way as to be dispersed and the console 110 executes defective pixel correction processing that generates pixel data of radiographic images in the positions where the radiation detecting pixels 32A are placed by interpolation using pixel data that has been obtained by the radiographic image acquiring pixels 32B positioned around those radiation detecting pixels 32A.

Additionally, in order to detect the state of application of the radiation, in the radiation detector 20, as shown in FIG. 5, direct read-out lines 38, to which connecting portions between the capacitors 9 and the thin-film transistors 10 in the radiation detecting pixels 32A are connected and which are for directly reading out the electric charges stored in those capacitors 9, are disposed extending in the one direction (the row direction). In the radiation detector 20 pertaining to the present exemplary embodiment, one direct read-out line 38 is allocated with respect to plural radiation detecting pixels 32A arranged side by side in the one direction, and the connecting portions between the capacitors 9 and the thin-film transistors 10 in those plural radiation detecting pixels 32A are connected to a common (single) direct read-out line 38.

In the present exemplary embodiment, the holding units 162 and 166 are configured in such a way that the angle of inclination of the grid 46 with respect to the electronic cassette 40 is changeable. The configurations of the holding units 162 and 166 will be described below with reference to FIG. 6A and FIG. 6B. Since the configurations of the holding units 162 and 166 are the same, only the configuration of the holding unit 166 will be described.

As shown in FIG. 6A and FIG. 6B, the holding unit 166 is equipped with a first holding unit 165A that fixedly holds the electronic cassette 40 and a second holding unit 165B that fixedly holds the grid 46.

The first holding unit 165A is disposed fixed to a housing of the holding unit 166, and the second holding unit 165B is configured so as to be rotatable in the direction of arrow A in FIG. 6A about the center portion in a plan view. Consequently, the holding unit 166 can change the relative angle between the electronic cassette 40 and the grid 46 in a state in which the holding unit 166 is holding the electronic cassette 40 and the grid 46.

A later-described motor 162A is disposed in the holding unit 162 and a later-described motor 166A is disposed in the holding unit 166 (see FIG. 9 for both motors). The second holding units 165B of each of the holding units 162 and 166 are rotated by the corresponding motors.

Figure 7:
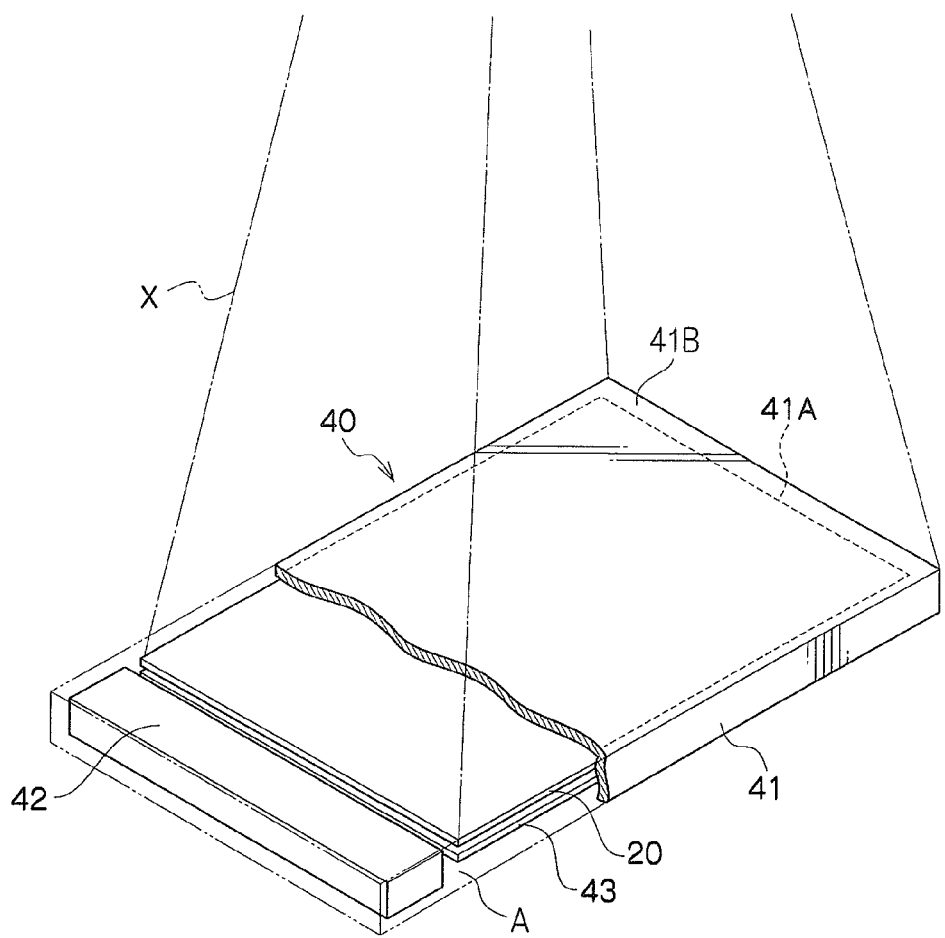
FIG. 7 is a perspective view showing the configuration of an electronic cassette pertaining to the exemplary embodiment.

Next, the configuration of the electronic cassette 40 pertaining to the present exemplary embodiment will be described. FIG. 7 is a perspective view showing the configuration of the electronic cassette 40.

As shown in FIG. 7, the electronic cassette 40 is equipped with a housing 41 that is formed from a material that allows radiation to pass through, and the electronic cassette 40 is given a waterproof and airtight structure. When the electronic cassette 40 is used in an operating room or the like, there is the concern that blood or other contaminants may adhere to the electronic cassette 40. Therefore, by giving the electronic cassette 40 a waterproof and airtight structure and disinfecting the electronic cassette 40 as needed, the single electronic cassette 40 can be used repeatedly.

A space A that accommodates various parts is formed inside the housing 41. The radiation detector 20, which detects the radiation X that has passed through the subject, and a lead plate 43, which absorbs backscattered rays of the radiation X, are disposed in this order inside the space A from an irradiated surface side of the housing 41 to which the radiation X is applied.

In the electronic cassette 40, the region corresponding to the disposed position of the radiation detector 20 in one surface of the tabular shape of the housing 41 is configured as a quadrilateral imaging region 41A that is capable of detecting the radiation. The surface having the imaging region 41A of the housing 41 is configured as a top plate 41B of the electronic cassette 40. In the electronic cassette 40, the radiation detector 20 is placed in such a way that the TFT substrate 30 is at the top plate 41B side, and the radiation detector 20 is adhered to the inner surface of the top plate 41B (the surface of the top plate 41B at the opposite side of the surface on which the radiation is made incident) in the housing 41.

As shown in FIG. 7, a case 42 that accommodates a later-described cassette controller 58 and a later-described power source unit 70 (see FIG. 9 for both) is placed at one end side of the interior of the housing 41 in a position that does not overlap with the radiation detector 20 (outside the range of the imaging region 41A).

The case 41 is configured by carbon fiber, aluminum, magnesium, bionanofibers (cellulose microfibrils), or a composite material, for example, in order to make the entire electronic cassette 40 lightweight.

As the composite material, for example, a material including reinforced fiber resin is used, and carbon, cellulose, or the like is included in the reinforced fiber resin. Specifically, as the composite material, carbon fiber reinforced plastic (CFRP), a composite material with a structure where a foam material is sandwiched by CFRP, or a composite material in which the surface of a foam material is coated with CFRP can be used. In the present exemplary embodiment, a composite material with a structure where a foam material is sandwiched by CFRP is used. Thereby, the strength (rigidity) of the housing 41 can be raised compared to a case in which the housing 41 is configured by a carbon alone.

Figure 8:
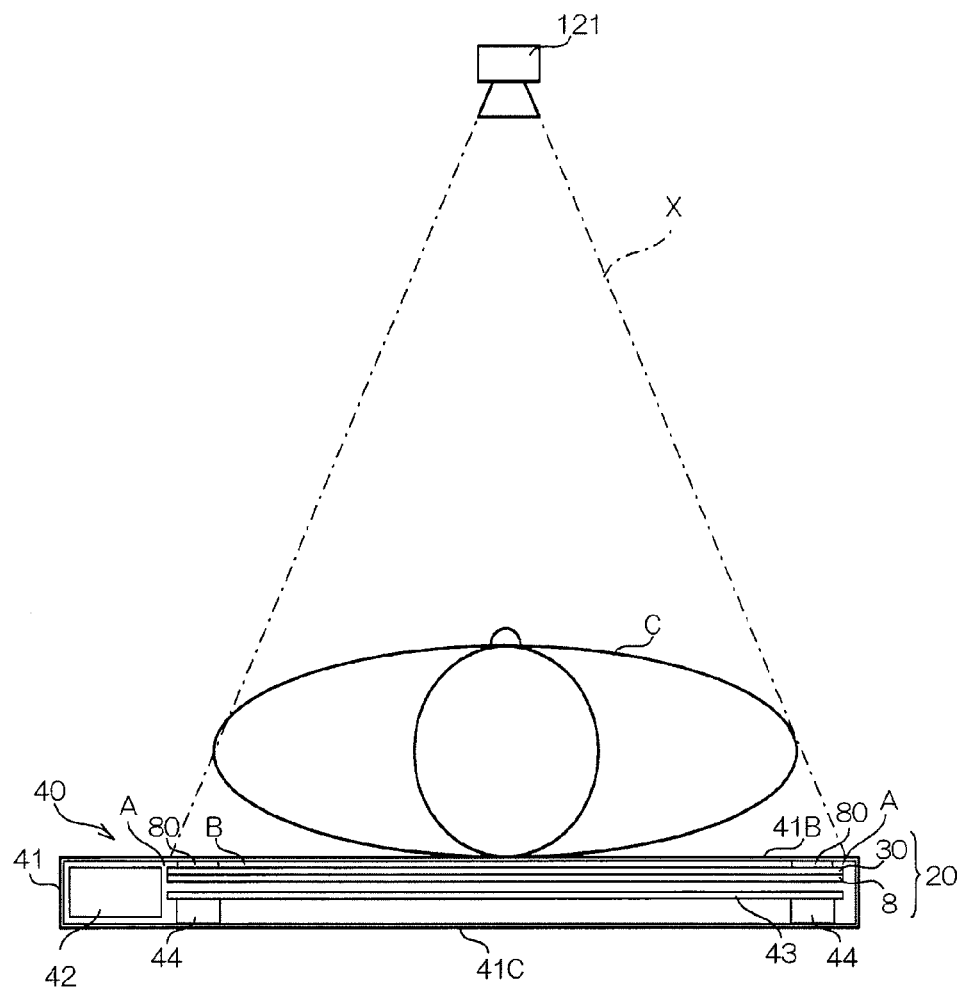
FIG. 8 is a cross-sectional side view showing the configuration of the electronic cassette pertaining to the exemplary embodiment.

As shown in FIG. 8, inside the housing 41, support members 44 are disposed on the inner surface of a back surface 41C opposing the top plate 41B. The radiation detector 20 and the lead plate 43 are placed in this order in the application direction of the radiation X between the support members 44 and the top plate 41B. The support members 44 are configured by a foam material, for example, from the standpoint of reducing weight and the standpoint of absorbing dimensional deviations, and the support members 44 support the lead plate 43. In FIG. 8, illustration of the grid 46 is omitted in order to avoid confusion.

As shown in FIG. 8, adhesive members 80 that detachably adhere the TFT substrate 30 of the radiation detector 20 are disposed at the inner surface of the top plate 41B. Double-sided tape, for example, can be used as the adhesive members 80. In this case, the double-sided tape is formed in such a way that the adhesive force of one adhesive surface is stronger than that of the other adhesive surface.

Specifically, the surface having a weak adhesive force (weak adhesive surface) is set to have a 180-degree peel strength equal to or less than 1.0 N/cm. The surface having a strong adhesive force (strong adhesive surface) contacts the top plate 41B, and the weak adhesive surface contacts the TFT substrate 30. Because of this configuration, the thickness of the electronic cassette 40 can be made thin compared to a case in which the radiation detector 20 is fixed to the top plate 41B by, for example, fixing members such as screws. Further, even if the top plate 41B deforms due to a shock or a load, the radiation detector 20 follows the deformation of the top plate 41B which has high rigidity, so only deformation of large curvature (a gentle curve) arises and the potential for the radiation detector 20 to break due to localized deformation of low curvature will be low. Moreover, the radiation detector 20 contributes to improving the rigidity of the top plate 41B.

In this way, in the electronic cassette 40, since the radiation detector 20 is adhered to the inner surface of the top plate 41B of the housing 41, the housing 41 is separable into two between the top plate 41B side and the back surface 41C side, and the housing 41 may be separated into two of the top plate 41B side and the back surface 41C side when the radiation detector 20 is adhered to the top plate 41B or when the radiation detector 20 is detached from the top plate 41B.

In the present exemplary embodiment, the adhesion of the radiation detector 20 to the top plate 41B does not have to be performed in a clean room or the like. The reason is because, even if foreign materials such as metal fragments that absorb radiation have been incorporated between the radiation detector 20 and the top plate 41B, the foreign materials can be removed by detaching the radiation detector 20 from the top plate 41B.

Next, the configurations of relevant portions of an electrical system of the imaging system 104 pertaining to the present exemplary embodiment will be described with reference to FIG. 9.

Figure 9:
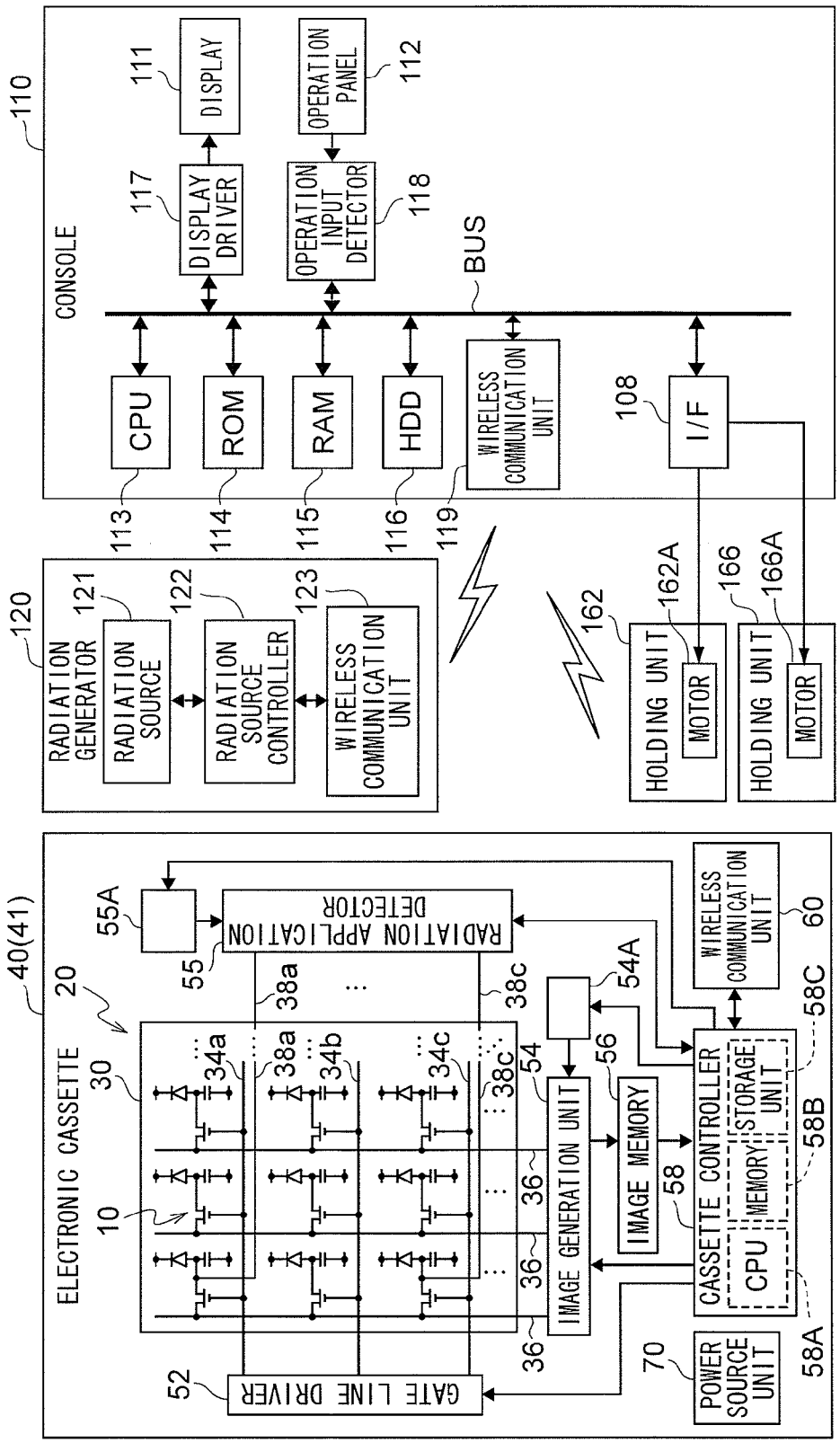
FIG. 9 is block diagram showing the configurations of main portions of an electrical system of the radiographic image capturing system pertaining to the exemplary embodiment.

As shown in FIG. 9, in the radiation detector 20 built into the electronic cassette 40, a gate line driver 52 is placed on one side of two sides adjacent to each other, and an image generation unit 54 is placed on the other side. The individual gate lines 34 (in FIG. 9, these are individually indicated as gate lines 34a, 34b, . . . , and these reference signs will be used as needed) of the TFT substrate 30 are connected to the gate line driver 52, and the individual data lines 36 of the TFT substrate 30 are connected to the image generation unit 54.

An image memory 56, a cassette controller 58, and a wireless communication unit 60 are disposed inside the housing 41.

The thin-film transistors 10 of the TFT substrate 30 are sequentially switched on in row units by signals supplied via the gate lines 34 from the gate line driver 52, and the electric charges that have been read out by the thin-film transistors 10 switched to an on-state are transmitted through the data lines 36 as electric signals and are inputted to the image generation unit 54. Thus, the electric charges are sequentially read out in row units, and a two-dimensional radiographic image can be acquired.

Figure 10:
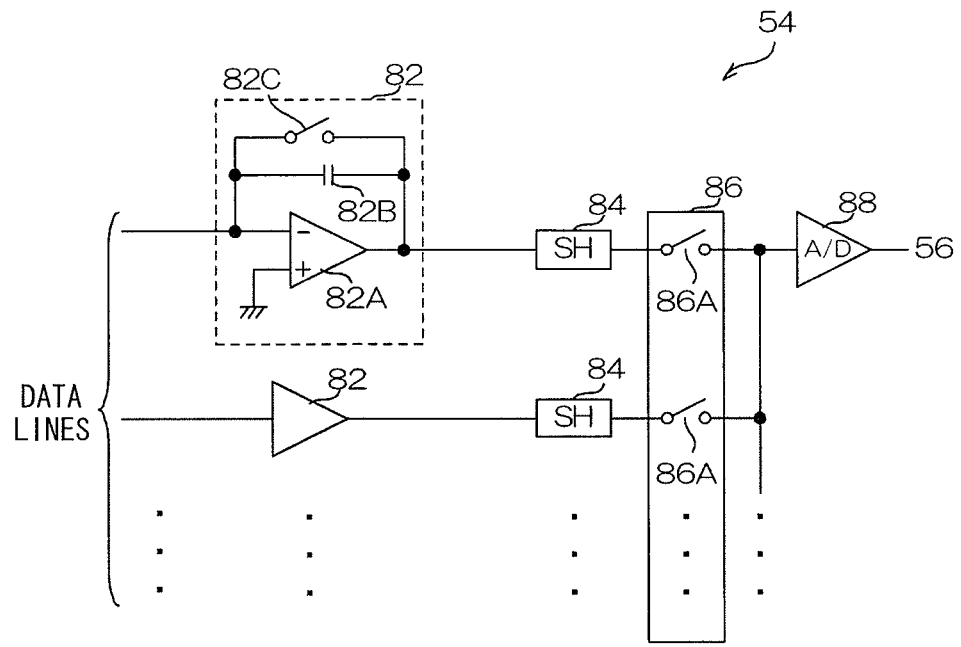
FIG. 10 is a circuit diagram showing the configuration of an image generation unit pertaining to the exemplary embodiment.

Here, the configuration of the image generation unit 54 pertaining to the present exemplary embodiment will be described. FIG. 10 is a circuit diagram showing the configuration of the image generation unit 54.

As shown in FIG. 10, the image generation unit 54 is equipped with variable gain pre-amplifiers (charge amplifiers) 82 and sample-and-hold circuits 84 in correspondence to each of the data lines 36.

Each of the variable gain pre-amplifiers 82 includes an operational amplifier (op-amp) 82A whose positive input end is grounded, a capacitor 82B that is connected in parallel between the negative input end and the output end of the op-amp 82A, and a reset switch 82C. The reset switches 82C are switched by the cassette controller 58.

Further, the image generation unit 54 is equipped with a multiplexer 86 and an analog-to-digital (A/D) converter 88. The sample timings of the sample-and-hold circuits 84 and the select output resulting from switches 86A disposed in the multiplexer 86 are also switched by the cassette controller 58.

When detecting a radiographic image, the cassette controller 58 first switches the reset switches 82C of the variable gain pre-amplifiers 82 to an on-state for a predetermined duration to thereby discharge the electric charges that had been stored in the capacitors 82B.

As a result of the radiation X being applied, the electric charges stored in the capacitors 9 of the radiographic image acquiring pixels 32B are transmitted through the connected data lines 36 as electric signals as a result of the connected thin-film transistors 10 being switched to an on-state, and the electric signals that have been transmitted through the data lines 36 are amplified at a predetermined gain by the corresponding variable gain pre-amplifiers 82.

After performing the discharge, the cassette controller 58 drives the sample-and-hold circuits 84 for a predetermined duration to thereby cause the sample-and-hold circuits 84 to hold the signal levels of the electric signals amplified by the variable gain pre-amplifiers 82.

The signal levels held in the sample-and-hold circuits 84 are sequentially selected by the multiplexer 86 in accordance with the control by the cassette controller 58 and are converted from analog to digital by the A/D converter 88, whereby image data representing the captured radiographic image are generated.

The electronic cassette 40 is equipped with a power source 54A that supplies power for driving to the image generation unit 54. The power source 54A is configured by a DC-DC converter whose power input end is connected to a later-described power source unit 70. The output end of the DC-DC converter is connected to the variable gain pre-amplifiers 82, the sample-and-hold circuits 84, the multiplexer 86, and the A/D converter 88 of the image generation unit 54.

The cassette controller 58 is connected to the control input end of the power source 54A. The start and stop of the supply of power from the power source 54A are controlled by the cassette controller 58.

The image memory 56 is connected to the image generation unit 54. The image data outputted from the A/D converter 88 of the image generation unit 54 are sequentially stored in the image memory 56. The image memory 56 has a storage capacity that is capable of storing image data for a predetermined number of frames' worth of radiographic images. Each time radiographic imaging is performed, the image data obtained by the imaging are sequentially stored in the image memory 56.

The image memory 56 is also connected to the cassette controller 58. The cassette controller 58 includes a microcomputer, which is equipped with a central processing unit (CPU) 58A, a memory 58B including a read-only memory (ROM) and a random access memory (RAM), and a nonvolatile storage unit 58C including a flash memory or the like, and controls the actions of the entire electronic cassette 40.

Moreover, the wireless communication unit 60 is connected to the cassette controller 58. The wireless communication unit 60 is adapted to a wireless local area network (LAN) standard represented by IEEE (Institute of Electrical and Electronics Engineers) 802.11a/b/g/n or the like and controls the transmission of various types of information (data) between the electronic cassette 40 and external devices by wireless communication. Via the wireless communication unit 60, the cassette controller 58 is made capable of wireless communication with external devices such as the console 110 that performs control relating to radiographic imaging and is made capable of transmitting and receiving various types of data to and from the console 110 and the like.

Further, a power source unit 70 is disposed in the electronic cassette 40. The various circuits and elements described above (the gate line driver 54, the image generation unit 54, the image memory 56, the wireless communication unit 60, the microcomputer functioning as the cassette controller 58, etc.) are actuated by power supplied from the power source unit 70. The power source unit 70 has a built-in battery (a rechargeable secondary battery) so as to not impair the portability of the electronic cassette 40, and the power source unit 70 supplies power to the various circuits and elements from the charged battery. In FIG. 9, illustration of wires connecting the various circuits and elements to the power source unit 70 is omitted.

In the radiation detector 20, a radiation application detector 55 is placed on the opposite side of the gate line driver 52 across the TFT substrate 30 in order to detect the state of application of the radiation. The individual direct read-out lines 38 (in FIG. 9, these are individually indicated as direct read-out lines 38a, 38c, . . . , and these reference signs will be used as needed) of the TFT substrate 30 are connected to the radiation application detector 55.

Figure 11:
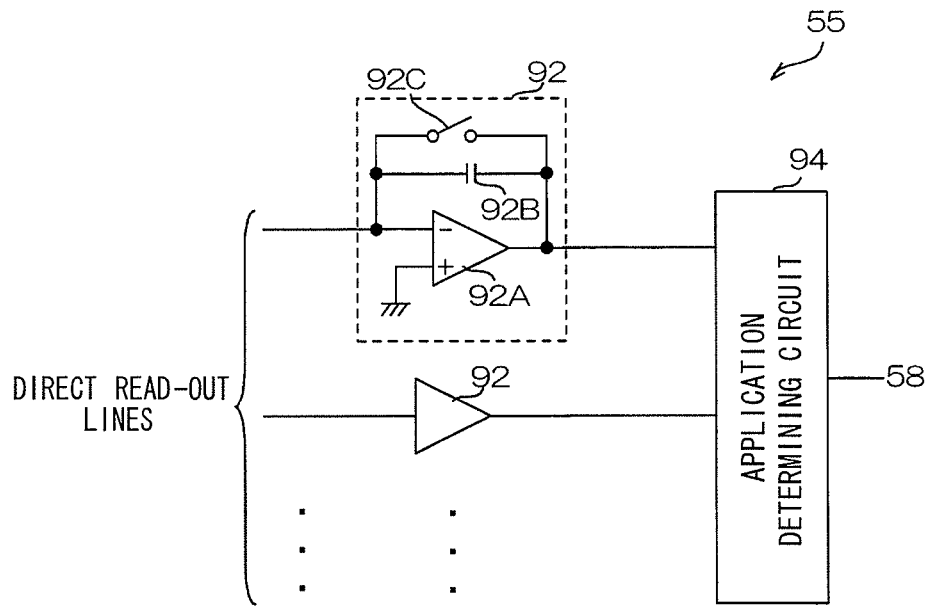
FIG. 11 is a circuit diagram showing the configuration of a radiation application detecting unit pertaining to the exemplary embodiment.

Here, the configuration of the radiation application detector 55 pertaining to the present exemplary embodiment will be described. FIG. 11 is a circuit diagram showing the configuration of the radiation application detector 55.

As shown in FIG. 11, the radiation application detector 55 is equipped with variable gain pre-amplifiers (charge amplifiers) 92 in correspondence to each of the direct read-out lines 38 connected to the radiation detecting pixels 32A.

Each of the variable gain pre-amplifiers 92 includes an operational amplifier (op-amp) 92A whose positive input side is grounded, a capacitor 92B that is connected in parallel between the negative input side and the output side of the op-amp 92A, and a reset switch 92C. The reset switches 92C are switched by the cassette controller 58.

Further, the radiation application detector 55 is equipped with an application determining circuit 94 whose input end is connected to the output ends of the variable gain pre-amplifiers 92 and whose output end is connected to the cassette controller 58.

When detecting the state of application of the radiation, the cassette controller 58 first switches the reset switches 92C of the variable gain pre-amplifiers 92 to an on-state for a predetermined duration to thereby discharge the electric charges that had been stored in the capacitors 92B.

The electric charges stored in the capacitors 9 of the radiation detecting pixels 32A as a result of the radiation X being applied are transmitted through the connected direct read-out lines 38 as electric signals, and the electric signals that have been transmitted through the direct read-out lines 38 are amplified at a predetermined gain by the corresponding variable gain pre-amplifiers 92 and are inputted to the application determining circuit 94.

The application determining circuit 94 determines, on the basis of the electric signals inputted from the variable gain pre-amplifiers 92, whether or not application of the radiation has been started by acquiring the dose of the radiation X (hereinafter called "radiation dose") that has been applied from the radiation source 121 and determining whether or not the radiation dose has reached a predetermined first threshold value. The application determining circuit 94 outputs first determination result information (data) indicating the determination result to the cassette controller 58.

Further, the application determining circuit 94 determines whether or not application of the radiation has been ended by determining whether or not the radiation dose has become less than a predetermined second threshold value. The application determining circuit 94 outputs second determination result information (data) indicating the determination result to the cassette controller 58.

When the application determining circuit 94 determines whether or not application of the radiation has been started, the application determining circuit 94 outputs information indicating that application of the radiation has been started as the first determination result information in a case in which there exist, in the output signals from the variable gain pre-amplifiers 92, output signals in which the radiation dose represented by those output signals has reached the first threshold value.

Further, when the application determining circuit 94 determines whether or not application of the radiation has been ended, the application determining circuit 94 outputs information indicating that application of the radiation has been ended as the second determination result information in a case in which there exist, in the output signals from the variable gain pre-amplifiers 92, output signals in which the radiation dose represented by those output signals has become less than the second threshold value.

The electronic cassette 40 is equipped with a power source 55A that supplies power for driving to the radiation application detector 55. The power source 55A pertaining to the present exemplary embodiment is configured by a DC-DC converter whose power input end is connected to the power source unit 70. The output end of the DC-DC converter is connected to the variable gain pre-amplifiers 92 and the application determining circuit 94 of the radiation application detector 55.

Here, the cassette controller 58 is connected to the control input end of the power source 55A. The start of the supply of power and the stop of the supply of power from the power source 55A are controlled by the cassette controller 58.

As shown in FIG. 9, the console 110 is configured as a server computer and is equipped with a display 111, which displays operation menus, captured radiographic images, and so forth, and an operation panel 112, which is configured to include plural keys and by which various types of information (data) and operation instructions are inputted.

Further, the console 110 is equipped with a CPU 113 that controls the actions of the entire device, a ROM 114 in which various programs including a control program are stored beforehand, a RAM 115 that temporarily stores various types of data, a hard disk drive (HDD) 116 that stores and holds various types of data, a display driver 117 that controls the display of various types of information on the display 111, and an operation input detector 118 that detects states of operation with respect to the operation panel 112. Further, the console 110 is equipped with a wireless communication unit 119 and an interface (I/F) unit 108. The wireless communication unit 119 transmits and receives various types of information (data) such as later-described exposure conditions to and from the radiation generator 120 by wireless communication and also transmits and receives various types of information (data) such as image data to and from the electronic cassette 40 by wireless communication. The interface unit 108 is connected to the motor 162A disposed in the holding unit 162 and the motor 166A disposed in the holding unit 166 and drives these motors to rotate.

The CPU 113, the ROM 114, the RAM 115, the HDD 116, the display driver 117, the operation input detector 118, the wireless communication unit 119, and the interface unit 108 are connected to each other via a system bus. Consequently, the CPU 113 can access the ROM 114, the RAM 115, and the HDD 116, can control the display of various types of information on the display 111 via the display driver 117, can control the transmission and reception of various types of information (data) to and from the radiation generator 120 and the electronic cassette 40 via the wireless communication unit 119, and can control the driving of the motor 162A and the motor 166A to rotate via the interface unit 108. Further, the CPU 113 can grasp states of operation by a user with respect to the operation panel 112 via the operation input detector 118.

The radiation generator 120 is equipped with the radiation source 121, a wireless communication unit 123 that transmits and receives various types of information (data) such as the exposure conditions to and from the console 110, and a radiation source controller 122 that controls the radiation source 121 on the basis of the received exposure conditions.

The radiation source controller 122 is also configured to include a microcomputer and stores the received exposure conditions and so forth. The exposure conditions received from the console 110 include information such as tube voltage, tube current, and so forth. The radiation source controller 122 causes the radiation source 121 to apply the radiation X on the basis of the received exposure conditions.

The imaging system 104 pertaining to the present exemplary embodiment is provided with an angle adjusting function for adjusting the relative angle between the electronic cassette 40 and the grid 46 in order to prevent the generation of moiré fringes that are caused by the grid 46 and arise in radiographic images obtained by imaging by the electronic cassette 40. In the angle adjusting function pertaining to the present exemplary embodiment, the range of the relative angle is predetermined in accordance with the combination of the type of the electronic cassette 40 and the type of the grid 46 that are to be used.

Figure 12:
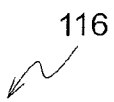
FIG. 12 is a schematic diagram showing the configuration of angle-of-rotation information pertaining to the exemplary embodiment.

For this reason, in the HDD 116 of the console 110, as an example, angle-of-rotation information schematically shown in FIG. 12 is stored beforehand.

As shown in FIG. 12, in the angle-of-rotation information, angular ranges representing ranges of the relative angle are stored beforehand per combination of type of electronic cassette and type of grid. In the imaging system 104, as the angular ranges per combination of type of electronic cassette and type of grid, ranges of the angle θ that satisfies $f_G' > \mu f_N'$ are derived using the spatial frequency $f_G'$ calculated on the basis of expression (7) and expression (8) described above and are stored beforehand in corresponding storage regions of the angle-of-rotation information. Here, for μ, a value that has been predetermined by an image quality evaluation or the like using human body signals obtained by actual radiographic images is used.

Next, the operation of the imaging system 104 will be described.

Figure 13:
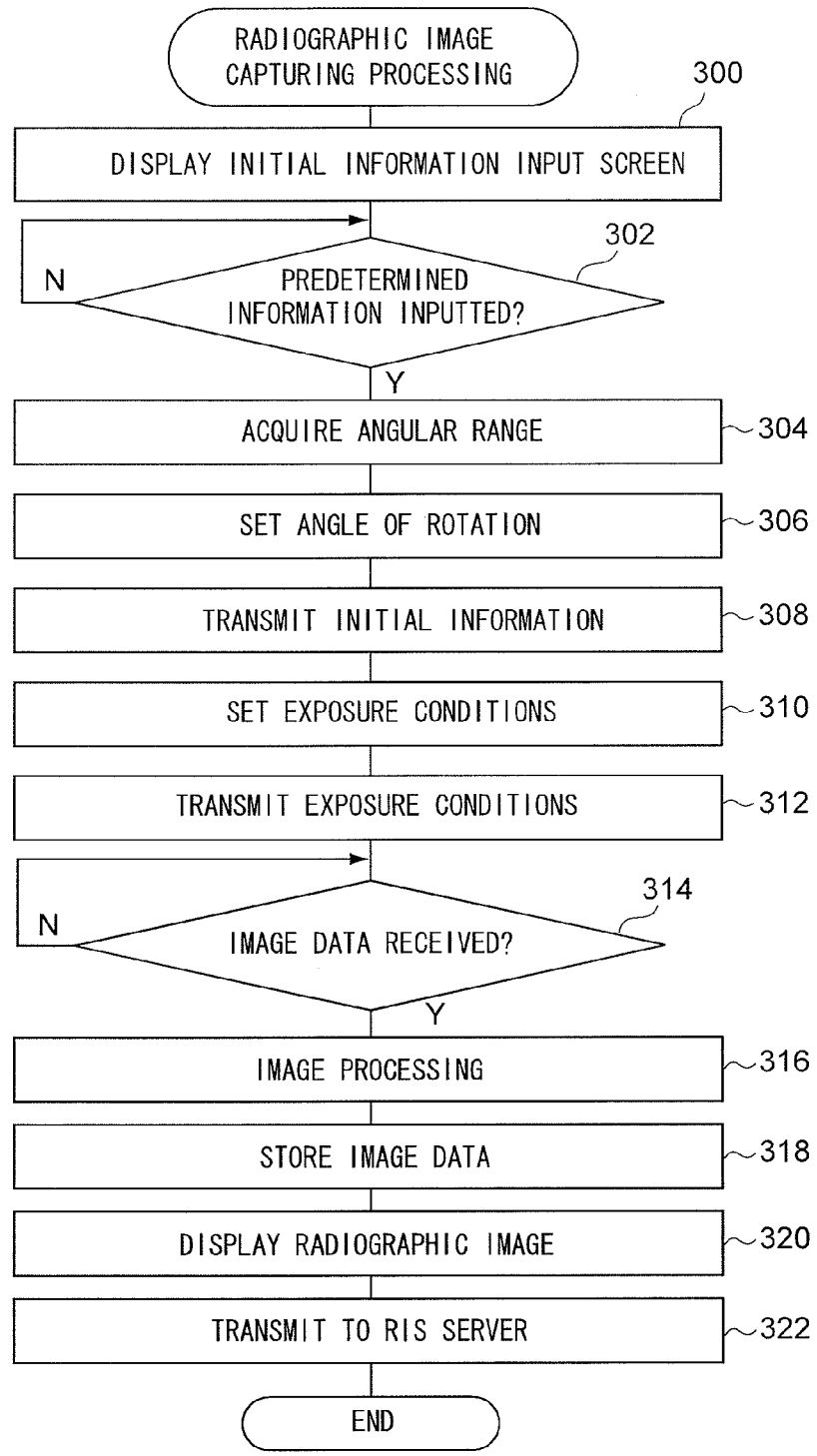
FIG. 13 is a flowchart showing a flow of processing by a radiographic image capturing program pertaining to the exemplary embodiment.

First, the operation of the console 110 when capturing a radiographic image will be described with reference to FIG. 13. FIG. 13 is a flowchart showing a flow of processing by a radiographic image capturing program that is executed by the CPU 113 of the console 110 when an instruction to execute the program has been inputted via the operation panel 112. This program is stored beforehand in a predetermined region of the ROM 114.

In step 300 of FIG. 13, the CPU 113 controls the display driver 117 so as to cause the display 111 to display a predetermined initial information input screen. In the next step 302, the CPU 113 waits for the input of predetermined information.

FIG. 14 shows an example of the initial information input screen that is displayed on the display 111 by the processing of step 300. As shown in FIG. 14, in the initial information input screen, there are displayed a message prompting the user to input the name of the subject on which radiographic imaging is to be performed, the imaging target site, the posture during imaging, the exposure conditions of the radiation X during imaging (in the present exemplary embodiment, the tube voltage, the tube current, and the duration of exposure when emitting the radiation X), and the types of the electronic cassette and the grid that are to be used. Input fields for inputting these pieces of information are also displayed.

After the initial information input screen shown in FIG. 14 is displayed on the display 111, the radiographer (user) may input the name of the subject serving as the imaging target, the imaging target site, the posture during imaging, the exposure conditions, the type of electronic cassette, and the type of grid into the corresponding input fields via the operation panel 112.

Then, the radiographer causes the holding unit 162 of the standing position stand 160 or the holding unit 166 of the lying position table 164 corresponding to the posture during imaging to hold the electronic cassette 40 and the grid 46 that are to be used, positions the radiation source 121 in the corresponding position, and thereafter positions the subject in a predetermined imaging position. Thereafter, the radiographer may designate, via the operation panel 112, the end button displayed in the neighborhood of the lower end of the initial information input screen. When the end button is designated by the radiographer, the determination in step 302 is affirmative and the processing moves to step 304.

In step 304, the CPU 113 acquires the angular range corresponding to the type of the electronic cassette and the type of the grid specified in the information inputted in the initial information input screen (hereinafter called "initial information") by reading the angular range from the angle-of-rotation information (see FIG. 12). In the next step 306, the CPU 113 controls the motor 162A in the case of imaging in the standing position or controls the motor 166A in the case of imaging in the lying position in such a way that the relative angle between the electronic cassette 40 and the grid 46 becomes an angle within the acquired angular range. In the imaging system 104, the angle in the center of the angular range is applied as the relative angle set by the processing of step 306, but the angle is not limited to this and may be any angle as long as the angle is within the angular range.

In the next step 308, the CPU 113 transmits the initial information to the electronic cassette 40 via the wireless communication unit 119. In the next step 310, the CPU 113 sets the exposure conditions by transmitting the exposure conditions included in the initial information to the radiation generator 120 via the wireless communication unit 119. In response to this, the radiation source controller 122 of the radiation generator 120 prepares for exposure in the received exposure conditions.

In the next step 312, the CPU 113 transmits instruction information instructing the start of exposure to the radiation generator 120 via the wireless communication unit 119.

In response to this, the radiation source 121 starts emitting the radiation X at the tube voltage, the tube current, and the duration of exposure corresponding to the exposure conditions that the radiation generator 120 received from the console 110. The radiation X emitted from the radiation source 121 passes through the subject and thereafter reaches the electronic cassette 40 via the grid 46.

After the cassette controller 58 of the electronic cassette 40 receives the initial information, the cassette controller 58 stands by (waits) until the first determination result information being outputted from the application determining circuit 94 becomes information indicating that application of the radiation has been started. Thereafter, the cassette controller 58 starts the action of capturing the radiographic image. Next, the electronic cassette 40 stands by (waits) until the second determination result information being outputted from the application determining circuit 94 becomes information indicating that application of the radiation has been ended. Thereafter, the electronic cassette 40 ends the imaging action.

Then, after the electronic cassette 40 ends the operation of capturing the radiographic image, the electronic cassette 40 transmits the image data obtained by the imaging to the console 110.

In the next step 314, the CPU 113 stands by until the image data are received from the electronic cassette 40. In the next step 316, the CPU 113 performs the defective pixel correction processing with respect to the received image data, thereafter performs moiré fringe removal processing, and thereafter executes image processing that performs various types of correction such as shading correction.

In the imaging system 104, as the moiré fringe removal processing, first the CPU 113 Fourier transforms the image data and detects the peak value (maximum value) of the spatial frequency in the two-dimensional frequency space obtained thereby. Then, the CPU 113 configures a two-dimensional band-stop filter that stops the passage of a predetermined frequency range including the detected peak value, and the CPU 113 performs filtering processing with respect to the image data using that filter.

Instead of the two-dimensional band-stop filter, a two-dimensional high-pass filter can also be applied, but a two-dimensional band-stop filter is more preferred in order to avoid as much as possible side effects caused by the filtering processing with respect to the radiographic image. Further, in the imaging system 104, as the predetermined frequency range, centering on the spatial frequency of the detected peak value, a range that does not include the spatial frequency of human body signals in a two-dimensional frequency space is applied.

In the next step 318, the CPU 113 stores in the HDD 116 the image data on which the image processing has been performed (hereinafter called "corrected image data"). In the next step 320, the CPU 113 controls the display driver 117 so as to display the radiographic image represented by the corrected image data on the display 111 for checking and so forth.

In the next step 322, the CPU 113 transmits the corrected image data to the RIS server 150 via the in-hospital network 102. Thereafter, the CPU 113 ends the radiographic image capturing program. The corrected image data that have been transmitted to the RIS server 150 are stored in the database 150A so that doctors can read the captured radiographic image and make a diagnosis.

Figure 15:
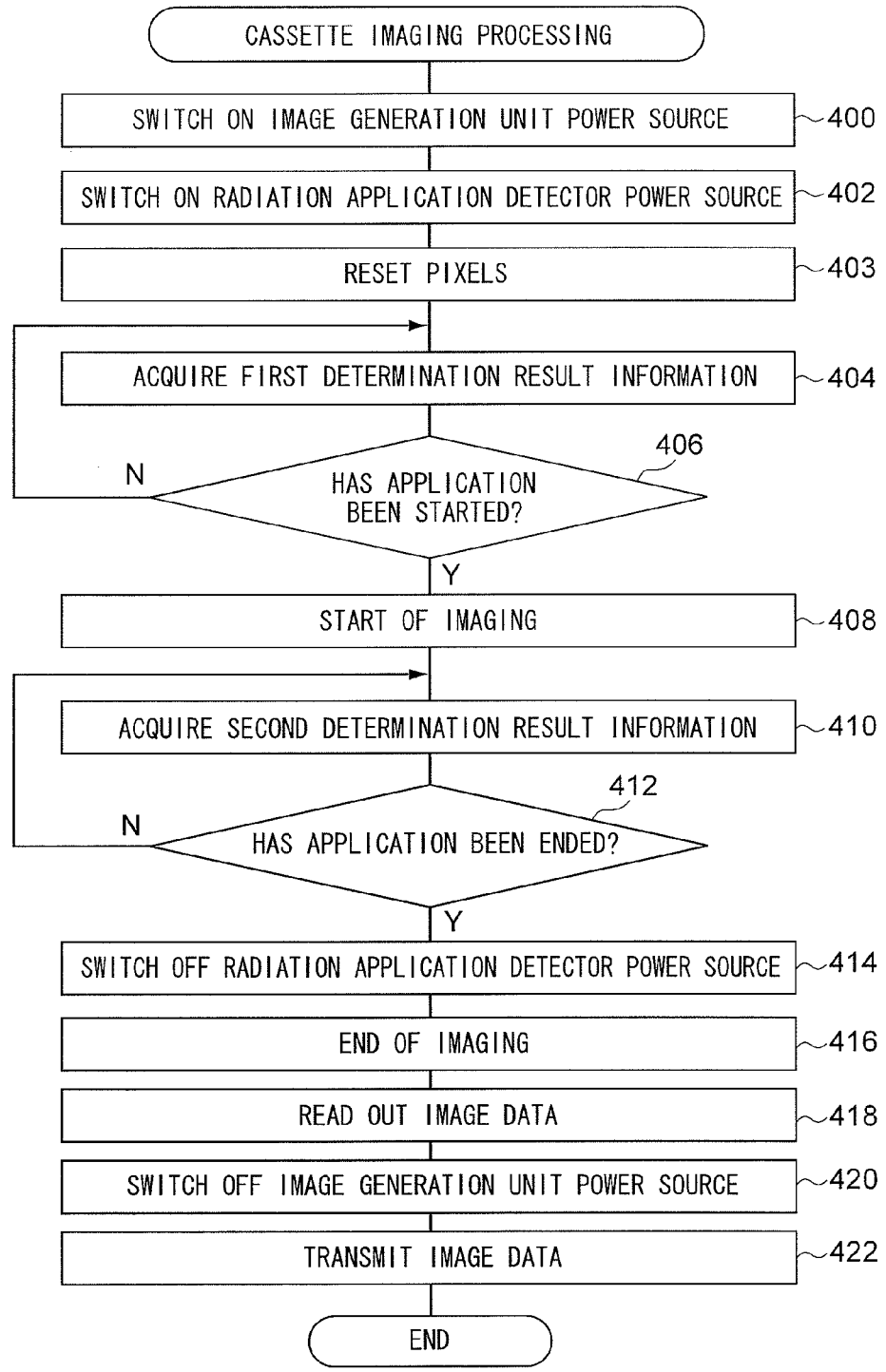
FIG. 15 is a flowchart showing a flow of processing by a cassette imaging program pertaining to the exemplary embodiment.

Next, the operation of the electronic cassette 40 after receiving the initial information from the console 110 will be described with reference to FIG. 15. FIG. 15 is a flowchart showing a flow of processing by a cassette imaging program that is executed by the CPU 58A in the cassette controller 58 of the electronic cassette 40 at this time. This program is stored beforehand in a predetermined region of the memory 58B.

In step 400 of FIG. 15, the CPU 58A controls the power source 54A so as to start supplying power from the power source 54A to the image generation unit 54. Thereafter, in the next step 402, the CPU 58A controls the power source 55A so as to start supplying power from the power source 55A to the radiation application detector 55. In the next step 403, the CPU 58A controls the gate line driver 52, causes on-signals to be outputted sequentially one line at a time from the gate line driver 52 to the gate lines 34a, 34b, 34c, . . . , and discharges the electric charges stored in the capacitors 9 in the pixels 32 of the radiation detector 20 to thereby reset the pixels 32 of the radiation detecting pixels 32A and the radiographic image acquiring pixels 32B. The action of resetting the pixels 32 that is performed by the processing of step 403 may be performed only one time or may be repeated plural times.

In the next step 404, the CPU 58A acquires the first determination result information from the application determining circuit 94. In the next step 406, the CPU 58A determines whether or not the acquired first determination result information is information indicating that application of the radiation has been started. If the determination is negative, the CPU 58A returns to step 404. If the determination is affirmative, the processing moves to step 408.

In step 408, the CPU 58A starts the operation of capturing the radiographic image by starting the storage of electric charges in the capacitors 9 in the pixels 32 of the radiation detector 20.

In the next step 410, the CPU 58A acquires the second determination result information from the application determining circuit 94. In the next step 412, the CPU 58A determines whether or not the acquired second determination result information is information indicating that application of the radiation has been ended. In a case where the determination is negative, the processing returns to step 410. If the determination is affirmative, the processing moves to step 414.

In step 414, the CPU 58A controls the power source 55A so as to stop the supply of power from the power source 55A to the radiation application detector 55 that has been started by the processing of step 402. In the next step 416, the CPU 58A ends the imaging operation that has been started by the processing of step 408.

In the next step 418, the CPU 58A controls the gate line driver 52, causes on-signals to be outputted sequentially one line at a time from the gate line driver 52 to the gate lines 34a, 34b, 34c, . . . , and sequentially switches on one line at a time the thin-film transistors 10 connected to the gate lines 34.

In the radiation detector 20, when the thin-film transistors 10 connected to the gate lines 34 are sequentially switched on one line at a time, the electric charges stored in the capacitors 9 sequentially flow out one line at a time as electric signals to the data lines 36. The electric signals flowing out to the data lines 36 are converted into digital image data by the image generation unit 54, and the image data are stored in the image memory 56.

In step 418, the CPU 58A reads out the image data stored in the image memory 56. In the next step 420, the CPU 58A discharges residual electric charges after the read-out of the electric charges by the processing of step 418 has ended and/or the electric charges in which dark current has been stored in the capacitors 9 in the pixels 32 of the radiation detector 20 to thereby reset the pixels 32 of the radiation detecting pixels 32A and the radiographic image acquiring pixels 32B. Thereafter the CPU 58A controls the power source 54A so as to stop the supply of power from the power source 54A to the image generation unit 54 that has been started by the processing of step 400. In the next step 422, the CPU 58A transmits the image data that has been read out to the console 110 via the wireless communication unit 60. Thereafter, the CPU 58A ends the cassette imaging program.

In the electronic cassette 40, as shown in FIG. 8, the radiation detector 20 is built-in in such a way that the radiation X is applied from the TFT substrate 30 side.

Figure 16:
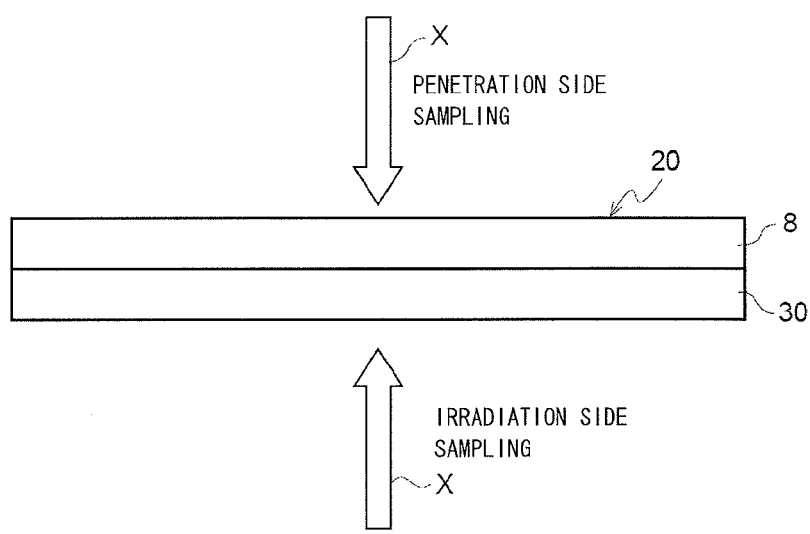
FIG. 16 is a cross-sectional side view for describing a radiographic image Irradiation Side Sampling (ISS) method and Penetration Side Sampling (PSS) method employed in a radiation detector.

Here, as shown in FIG. 16, in a case in which the radiation detector 20 is configured to adopt Penetration Side Sampling (PSS) method in which the radiation is applied from the side on which the scintillator 8 is formed and the radiographic image is read by the TFT substrate 30 disposed on the back surface side of the surface on which the radiation is made incident, light is emitted more strongly on the upper surface side of the scintillator 8 in FIG. 16 (the opposite side of the TFT substrate 30 side). Alternatively, in a case in which the radiation detector 20 is configured to adopt Irradiation Side Sampling (ISS) method in which the radiation is applied from the TFT substrate 30 side and the radiographic image is read by the TFT substrate 30 disposed on the front surface side of the surface on which the radiation is made incident, the radiation that has passed through the TFT substrate 30 is made incident on the scintillator 8, and the TFT substrate 30 side of the scintillator 8 more strongly emits light. Electric charges are generated by the light generated by the scintillator 8 in the sensor portions 13 disposed on the TFT substrate 30. Thus, since the emission position of the scintillator 8 with respect to the TFT substrate 30 is closer in a case in which the radiation detector 20 adopts the Irradiation Side Sampling method than in a case in which the radiation detector 20 adopts the Penetration Side Sampling method, the resolution of the radiographic image obtained by imaging is higher in the Irradiation Side Sampling method than in the Penetration Side Sampling method.

Further, in the radiation detector 20, the photoelectric conversion layer 4 is configured by an organic photoelectric conversion material, and virtually no radiation is absorbed by the photoelectric conversion layer 4. For this reason, in the radiation detector 20, the amount of radiation absorbed by the photoelectric conversion layer 4 is small even in a case in which the radiation passes through the TFT substrate 30 in the Irradiation Side Sampling method, so a drop in sensitivity with respect to the radiation can be suppressed. In the Irradiation Side Sampling method, the radiation reaches the scintillator 8 after passing through the TFT substrate 30. Therefore, by configuring the photoelectric conversion layer 4 of the TFT substrate 30 by an organic photoelectric conversion material as in the present exemplary embodiment, there is virtually no absorption of the radiation by the photoelectric conversion layer 4 and attenuation of the radiation can be kept small, so this configuration is suited to the Irradiation Side Sampling method.

Further, the amorphous oxide configuring the active layers 17 of the thin-film transistors 10 and the organic photoelectric conversion material configuring the photoelectric conversion layer 4 are both capable of being formed into films at a low temperature. For this reason, the substrate 1 can be formed by plastic resin, aramid, or bionanofibers in which there is little absorption of radiation. Since the amount of radiation absorbed is small in the substrate 1 formed in this way, a drop in sensitivity with respect to the radiation can be suppressed even in a case in which the radiation passes through the TFT substrate 30 in the Irradiation Side Sampling method.

Further, according to the present exemplary embodiment, as shown in FIG. 8, the radiation detector 20 is adhered to the top plate 41B inside the housing 41 in such a way that the TFT substrate 30 is at the top plate 41B side. In this configuration, in a case in which the substrate 1 is formed by plastic resin, aramid, or bionanofibers whose rigidity is high, the rigidity of the radiation detector 20 itself will be high, so the top plate 41B of the housing 41 can be formed thin. Further, in a case in which the substrate 1 is formed by plastic resin, aramid, or bionanofibers whose rigidity is high, the radiation detector 20 itself has flexibility, so the radiation detector 20 does not easily break even in a case in which shock has been applied to the imaging region 41A.

As described in detail above, in the present exemplary embodiment, the radiographic image capturing system acquires the angle of inclination of the grid, with respect to the array direction of the pixels of the radiation detector, with which the spatial frequency of moiré fringes generated by the absorbing members of the grid (the grid 46) in the radiographic image captured by the radiation detector (the radiation detector 20) is equal to or greater than a predetermined spatial frequency and executes predetermined processing for making the relative angle between the grid and the radiation detector the acquired angle of inclination. Therefore, the generation of moiré fringes can be easily prevented without limiting the configuration of the grid and the radiation detector.

Further, in the present exemplary embodiment, since the radiographic image capturing system applies the spatial frequency of human body signals as the predetermined spatial frequency, the generation of moiré fringes can be prevented more reliably.

Further, in the present exemplary embodiment, the radiographic image capturing system has a changing unit (the holding unit 162 and the holding unit 166) that changes the relative angle between the radiographic image capturing device and the grid, and the radiographic image capturing system executes, as the predetermined processing, processing that controls the changing unit in such a way that the relative angle becomes the acquired angle of inclination, Therefore, convenience can be improved compared to a case in which the relative angle between the radiographic image capturing device and the grid is set manually.

Moreover, in the present exemplary embodiment, the radiographic image capturing system identifies the spatial frequency of moiré fringes generated by the absorbing members in the radiographic image and performs image processing that removes, from the radiographic image, the component of the identified spatial frequency. Therefore, the generation of moiré fringes can be prevented more reliably.

The present invention has been described above using an exemplary embodiment, but the technical scope of the present invention is not limited to the scope described in the exemplary embodiment. Various changes or improvements can be made to the exemplary embodiment without departing from the gist of the invention, and the technical scope of the present invention also includes embodiments to which such changes or improvements have been made.

Further, the exemplary embodiment is not intended to limit the inventions pertaining to the claims, and it is not the case that all combinations of features described in the exemplary embodiment are essential to the solution of the present invention. The exemplary embodiment includes inventions of various stages, and various inventions can be extracted by appropriate combinations of the plural configural requirements disclosed. Even if several configural requirements are omitted from all the configural requirements disclosed in the exemplary embodiment, configurations from which those several configural requirements have been omitted can also be extracted as inventions as long as the same effects are obtained.

Figure 17A:
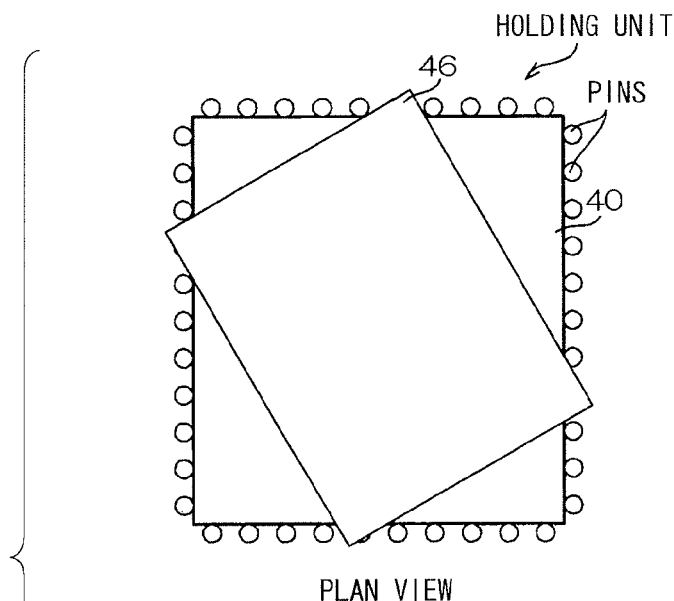
FIG. 17A is a plan view showing another example configuration of the holding unit pertaining to the exemplary embodiment.
Figure 17B:
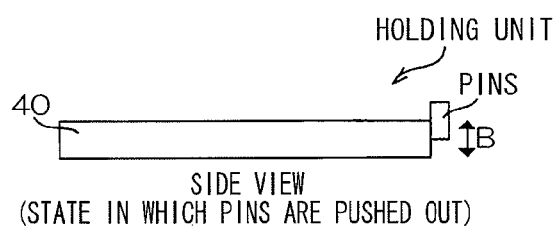
FIG. 17B is a side view showing a state in which pins are pushed out in the other example configuration of the holding unit.
Figure 17C:
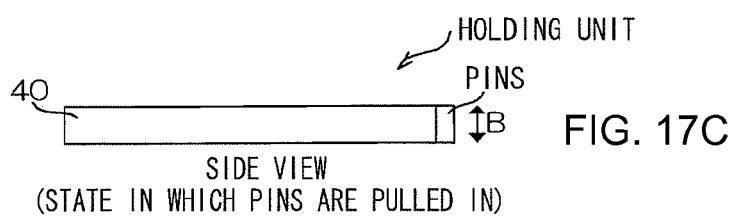
FIG. 17C is a side view showing a state in which the pins are pulled in the other example configuration of the holding unit.

For example, in the above exemplary embodiment, a case has been described in which the holding units 162 and 166 that employ a turntable system are applied as units for changing the relative angle between the electronic cassette 40 and the grid 46, but embodiments of the present invention are not limited to this. For example, as shown in FIG. 17A to FIG. 17C, an embodiment may be given a configuration in which units having plural pins that hold the periphery of the electronic cassette 40 at predetermined intervals and are capable of being pushed out and pulled in the direction of arrow B in FIG. 17B and FIG. 17C are applied as the holding units 162 and 166. In this case, the actions of pushing out and pulling in the pins are configured to be controllable by the CPU 113 of the console 110, and the pushed-out and pulled-in states of the pins are controlled in such a way that the grid 46 is placed on the top plate 41B side of the electronic cassette 40 at an angle within the angular range acquired from the angle-of-rotation information.

Figure 18A:
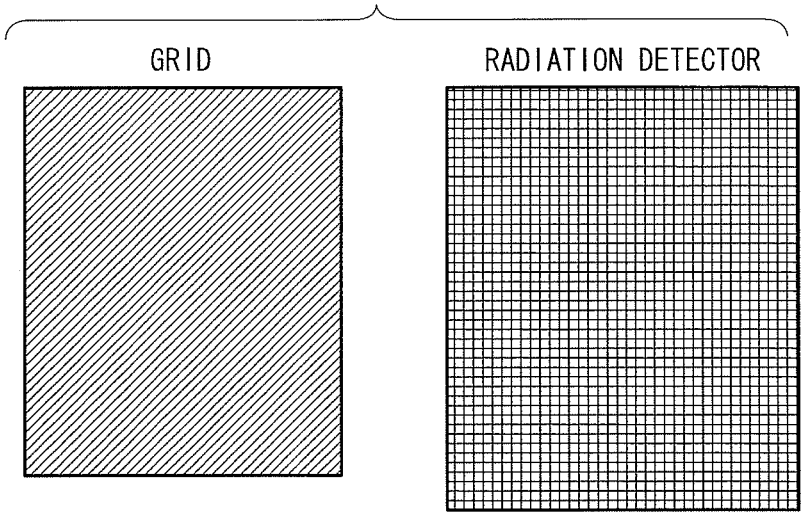
FIG. 18A and FIG. 18B are plan views showing other example configurations of a grid and the radiation detector pertaining to the exemplary embodiment.
Figure 18B:
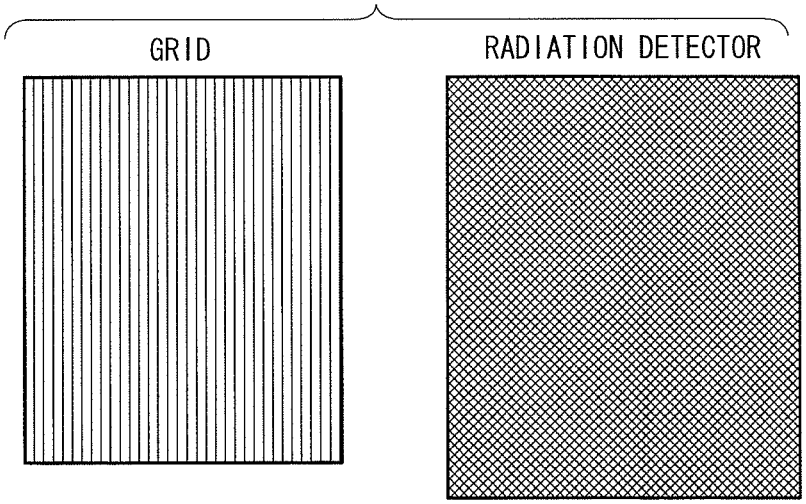

Further, in the above exemplary embodiment, a case has been described in which the grid 46 is inclined with respect to the electronic cassette 40, but embodiments of the present invention are not limited to this. An embodiment may also, for example, be given a configuration which, as shown in FIG. 18A, uses a grid in which the array direction of the radiation absorbing material is inclined in a diagonal direction or which, as shown in FIG. 18B, uses a radiation detector in which the pixels are arrayed in a diagonal direction and without the grid being inclined. In the latter case, it is easier to align the body axis of the subject and the direction of the grid, so it is easier to finely adjust the position of the radiation source in the grid line direction in accordance with the body length of the subject.

In this case, the effect that the user does not have to expend unnecessary time and effort is obtained and, although processing to convert an image in the diagonal direction to an image in the vertical and horizontal directions is necessary, high resolution can be imparted to the vertical and horizontal directions of the image. Technologies for creating radiation detectors with the TFTs inclined by 45 degrees are conventionally known, and this effect can be provided by combining such a technology with a grid. For example, in the case of mammography with the pixel spacing of the radiation detector is 125 [μm], an image corresponding to the pixel spacing of 80 [μm] can be made by this inclination.

Further, in the above exemplary embodiment, a case has been described in which the radiographic image capturing system executes, as the predetermined processing of the present invention, processing that controls the holding units 162 and 166 in such a way that the relative angle between the electronic cassette 40 and the grid 46 becomes the acquired angle of inclination, but embodiments of the present invention are not limited to this. For example, an embodiment may be given a configuration that executes processing that notifies the angle of inclination to a user.

Figure 19:
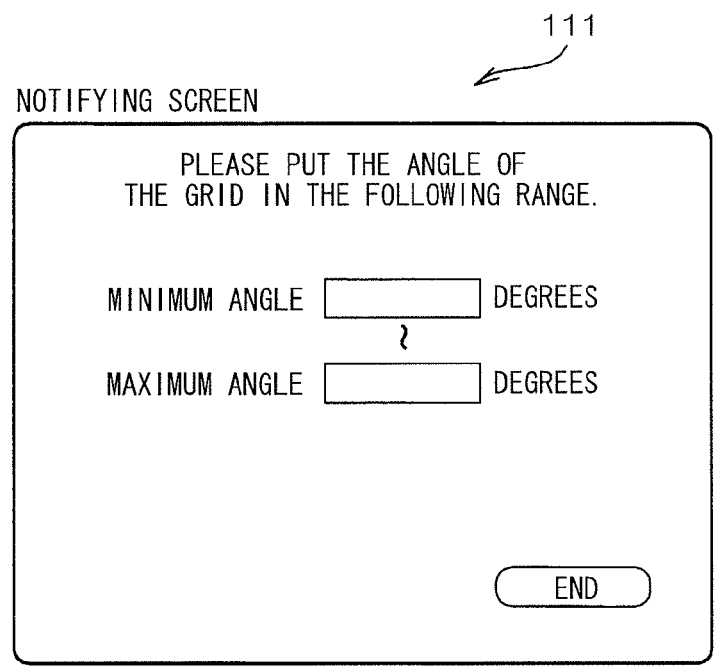
FIG. 19 is a schematic diagram showing the display of a notifying screen pertaining to the exemplary embodiment.
Figure 20:
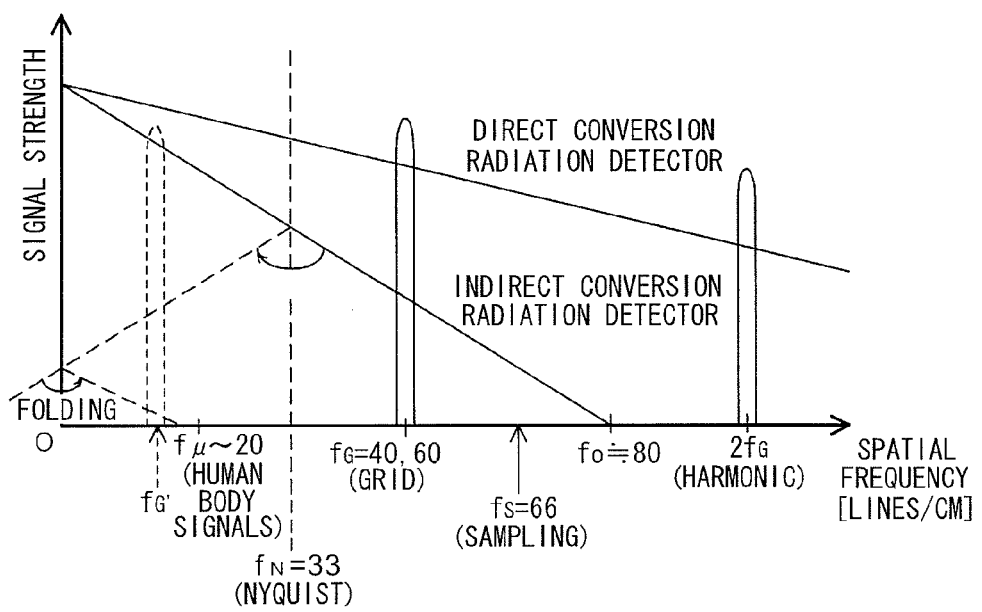
FIG. 20 is a diagram for describing the problem to be solved and is a graph showing an example of a one-dimensional frequency space.
Figure 21:
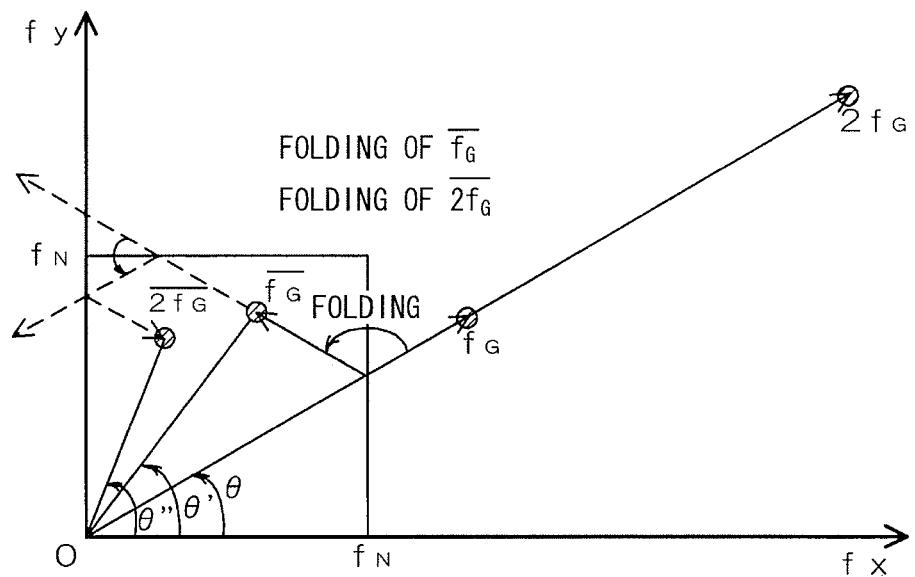
FIG. 21 is a diagram for describing the principle of the invention and is a graph showing an example of a two-dimensional frequency space.
Figure 22:
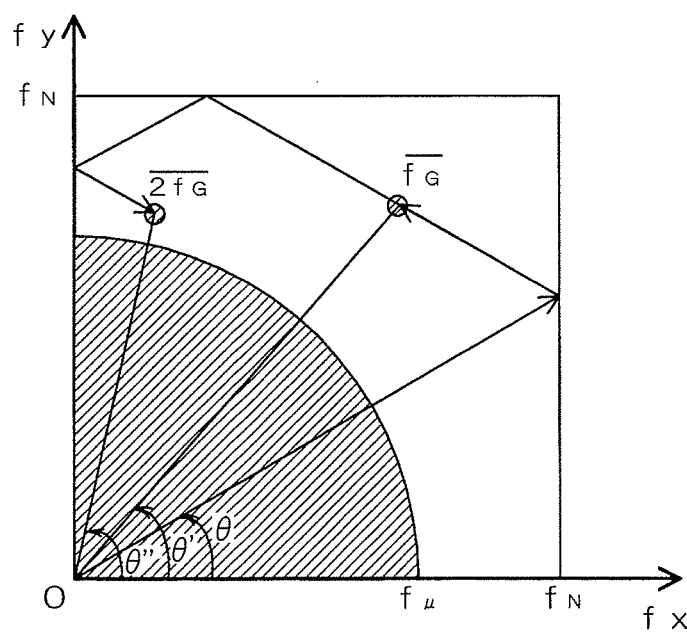
FIG. 22 is a diagram for describing the principle of the invention and is a graph showing another example of a two-dimensional frequency space.
Figure 23:
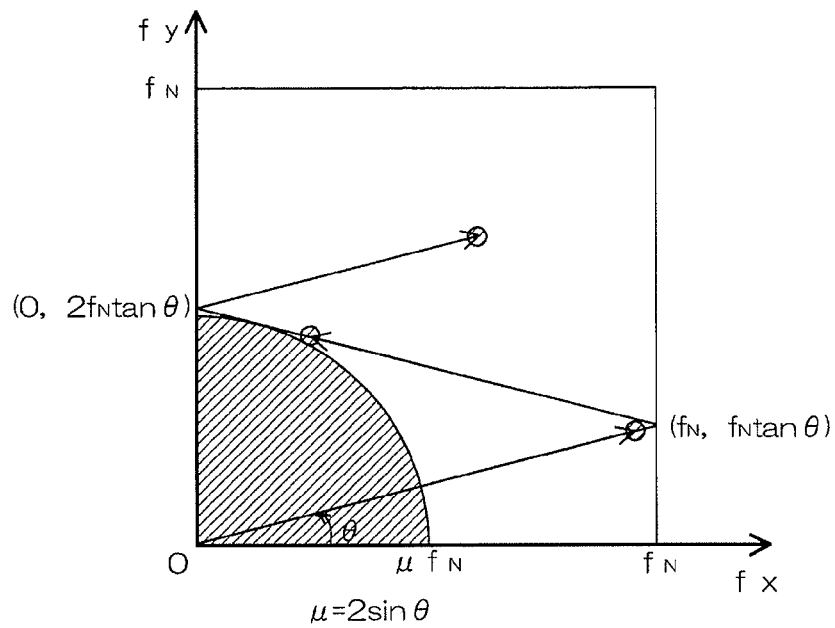
FIG. 23 is a diagram for describing the principle of the invention and is a graph showing another example of a two-dimensional frequency space.
Figure 24:
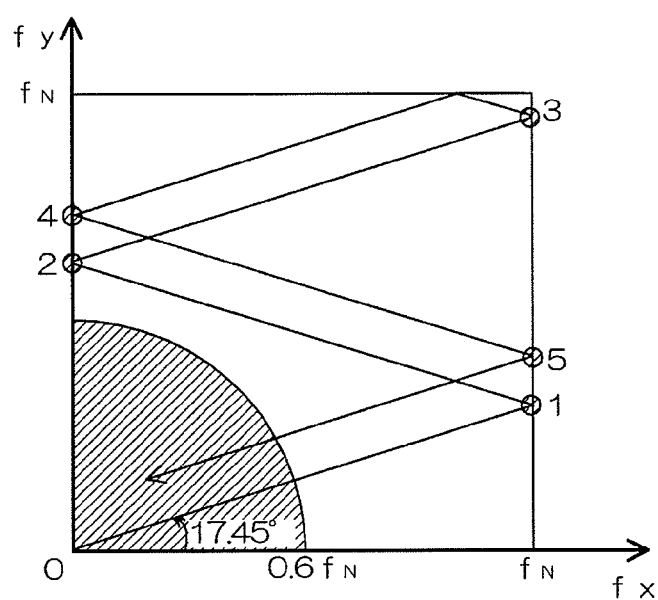
FIG. 24 is a diagram for describing the principle of the invention and is a graph showing another example of a two-dimensional frequency space.
Figure 25:
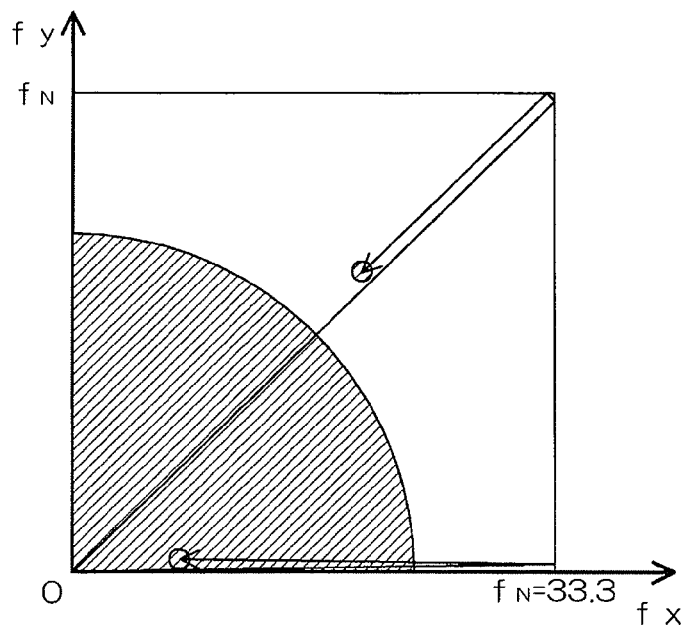
FIG. 25 is a diagram for describing the principle of the invention and is a graph showing another example of a two-dimensional frequency space.
Figure 26:
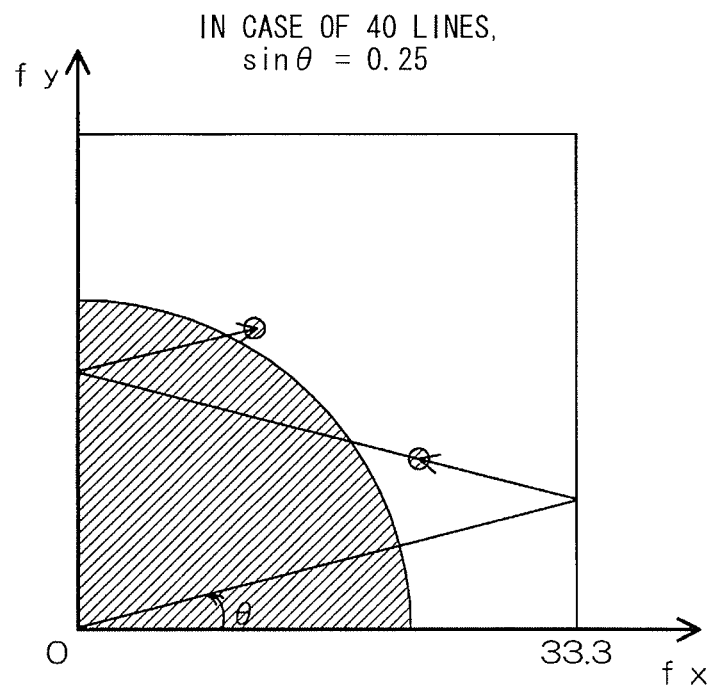
FIG. 26 is a diagram for describing the principle of the invention and is a graph showing another example of a two-dimensional frequency space.
Figure 27:
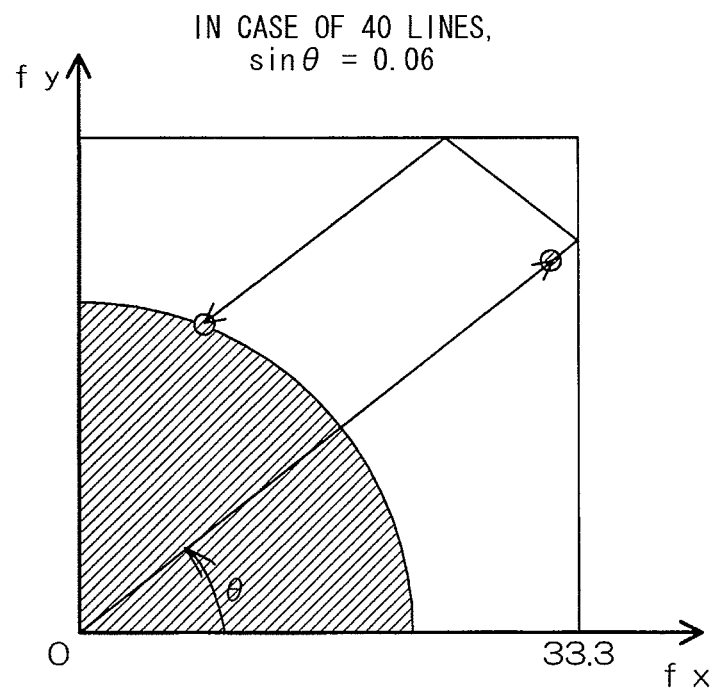
FIG. 27 is a diagram for describing the principle of the invention and is a graph showing another example of a two-dimensional frequency space.

FIG. 19 shows an example of a notifying screen in a case in which the angle of inclination is reported by the display 111 of the console 110 in this configuration. In this case, instead of the processing of step 306 by the radiographic image capturing program (see also FIG. 13), the radiographic image capturing system executes processing by which the display 111 displays the angular range acquired by the processing of step 304. In this case, the user can easily grasp the angle of inclination. In this case, since the displayed angular range is relatively wide and there is robustness in the installation angle of the grid, manual placement of the grid in an angle within the shown range is also possible.

Further, according to the above exemplary embodiment, since the angular range is determined if the electronic cassette and the grid that are to be used are determined, reproducibility in the case of manual placement can be raised by putting a mark in the position where the grid is to be disposed. In the electronic cassette, a reinforced jacket may be combined with a grid and, therefore, a rail portion (including a lock portion) on which a grid portion of the reinforced jacket and the electronic cassette relatively rotate may be attached to the reinforced jacket or a frame to which the electronic cassette diagonally attaches may be initially disposed on the reinforced jacket. In a case in which the peripheral portion of a relatively large-sized grid has become damaged, the damaged place can be cut and the grid can be used as a small-sized grid. At that time the grid can be diagonally cut and combined with in an electronic cassette or imaging table for use.

In phase imaging, there are cases in which a grid is installed diagonally, and by applying the above method, grids with a number of lines in which harmonics do not appear in the image or grids with a number of lines in which harmonics can be removed by image processing will be selectable.

Further, in the above exemplary embodiment, a case has been described in which angular ranges per combination of the type of the electronic cassette and the type of the grid are stored beforehand as the angle-of-rotation information (see FIG. 12) and the angle θ is acquired by reading out the corresponding angular range, but embodiments of the present invention are not limited to this. For example, an embodiment may be given a configuration in which an expression for calculating the spatial frequency $f_G'$ and the value of the ratio μ are stored beforehand and the angle θ is acquired by calculation using these values.

Further, in the above exemplary embodiment, a case has been described in which angular ranges per combination of the type of the electronic cassette and the type of the grid are stored beforehand and the angle θ is acquired by reading out the angular range corresponding to the type of the electronic cassette and the type of the grid that have been inputted, but embodiments of the present invention are not limited to this. For example, an embodiment may be given a configuration in which, in view of the fact that the optimum μ representing human body signals differs per imaging site, angular ranges per combination of the type of the electronic cassette, the type of the grid, and the type of the imaging sites are stored beforehand as the angle-of-rotation information, the type of the electronic cassette, the type of the grid, and the type of the imaging site are inputted by a user, and the angle θ is acquired by reading out the angular range corresponding to these types that have been inputted.

Further, in the above exemplary embodiment, a case has been described in which the holding units 162 and 166 are controlled in such a way that the relative angle between the electronic cassette 40 and the grid 46 becomes the acquired angle of inclination, but embodiments of the present invention are not limited to this. An embodiment may be given a configuration in which the type of the grid and the angle of inclination of that grid with which the spatial frequency of moiré fringes generated by the absorbing members of the grid 46 in the radiographic image can be made equal to or greater than a predetermined spatial frequency are acquired and the acquired type and angle of inclination of the grid are notified to a user.

Moreover, in this configuration, the embodiment may also be given a configuration in which the type and angle of inclination of the grid are acquired and notified per imaging site. The type and angle of inclination of the grid in this configuration can be obtained, as a combination of the type and angle of inclination of the grid per combination of the imaging site and the type of the electronic cassette, by using the spatial frequency $f_G'$ calculated on the basis of expression (7) and expression (8) described above to derive ones that satisfy $f_G' > \mu f_N$. The notification in this configuration may include notifying by a display device, by a speech producing unit such as a speaker, and by an image formation unit such as a printer.

According to this configuration, it will be easy to use dedicated grids or share identical grids in imaging rooms dedicated to the chest and imaging rooms dedicated to orthopedics, and as a result a less number of grids can be effectively used.

Further, in the above exemplary embodiment, since some of the pixels 32 disposed in the radiation detector 20 are used as the radiation detecting pixels 32A, it is preferred the adjacent radiation detecting pixels 32A adjacent to each other be spaced far enough apart from each other so that defective pixel correction processing can be implemented.

Further, in the above exemplary embodiment, a case has been described in which the radiation detecting pixels 32A are used for detecting the start of application of the radiation and the end of application of the radiation. However, embodiments of the present invention are not limited to this. An embodiment may be given a configuration in which the radiation detecting pixels 32A are used to determine the applied amount of the radiation and detect the timing of the proper applied amount by integrating or cumulatively adding the outputs of the variable gain pre-amplifiers 92 or to detect the exposure rate per unit time of the radiation that is dependent on the tube voltage and the tube current of the radiation source for exposure management in fluoroscopy or the like by determining the maximum value of the outputs of the variable gain pre-amplifiers 92.

Further, in the above exemplary embodiment, a case has been described in which the radiation detecting pixels 32A arranged side by side in the row direction in the radiation detector 20 are connected to common direct read-out lines 38. However, embodiments of the present invention are not limited to this. An embodiment may be given a configuration in which all the radiation detecting pixels 32A are separately connected to different direct read-out lines 38.

Further, in the above exemplary embodiment, a case has been described in which the supply of power to the radiation application detector 55 has started at the timing when the input of the initial information ended. However, embodiments of the present invention are not limited to this. An embodiment may be given a configuration in which, for example, a switch that is pressed by a user when emitting the radiation is disposed and the supply of power to the radiation application detector 55 is started at the timing when that switch is pressed.

Further, in the above exemplary embodiment, a case has been described in which the exposure conditions are set from the console 110 by the radiation generator 120 and the emission of the radiation by the radiation source 121 is performed when the start of exposure has been instructed. However, embodiments of the present invention are not limited to this. An embodiment may be given a configuration in which, for example, a switch that is operated by a user when causing the radiation generator 120 to start the emission of the radiation and when causing the radiation generator 120 to end the emission is disposed and control is performed by the radiation source controller 122 of the radiation generator 120 so as to start and end the emission of the radiation in accordance with operations with respect to the switch.

Further, in the above exemplary embodiment, a case has been described in which some of the pixels 32 disposed in the radiation detector 20 are used as the radiation detecting pixels 32A. However, embodiments of the present invention are not limited to this. For example, an embodiment may be given a configuration in which, as disclosed in Japanese Patent No. 4,217,443, the radiation detecting pixels 32A are layered in the radiation detector 20 as a separate layer from the pixels 32, or a configuration in which, as disclosed in Japanese Patent No. 4,217,506, radiation detecting elements that act in the same way as the radiation detecting pixels 32A are disposed separately from the pixels 32. In this case, since defective pixels do not arise, the quality of the radiographic image can be improved compared to the above-described exemplary embodiment.

Further, in the above exemplary embodiment, a case has been described in which the radiation detecting pixels 32A are used as dedicated pixels that detect radiation, but embodiments of the present invention are not limited to this. An embodiment may also be given a configuration in which the radiation detecting pixels 32A double as the radiographic image acquiring pixels 32B. A configuration disclosed in JP-A No. 2009-219538, in which the state of application of the radiation is detected on the basis of a change in the bias voltage flowing to each pixel can serve as an example of this configuration.

Further, in the above exemplary embodiment, a case has been described in which the sensor portions 13 are configured to include the organic photoelectric conversion material in which electric charge is generated as a result of receiving the light generated by the scintillator 8. However, embodiments of the present invention are not limited to this. An embodiment may be given a configuration that applies sensor portions configured without including the organic photoelectric conversion material as the sensor portions 13.

Further, in the above exemplary embodiment, a case has been described in which the radiation detector 20 and the case 42 accommodating the cassette controller 58 and the power source unit 70 are placed inside the housing 41 of the electronic cassette 40 in such a way as to not overlap with each other, but embodiments of the present invention are not limited to this. For example, the cassette controller 58 and the power source unit 70 may also be placed in such a way as to overlap the radiation detector 20.

Further, in the above exemplary embodiment, a case has been described in which communication is performed wirelessly between the electronic cassette 40 and the console 110 and between the radiation generator 120 and the console 110. However, embodiments of the present invention are not limited to this and may also be given a configuration in which, for example, communication between at least one of these is performed via wires.

Further, in the above exemplary embodiment, a case has been described in which X-rays are applied as the radiation. However, embodiments of the present invention are not limited to this and may also be given a configuration in which another form of radiation such as gamma rays is applied.

The configuration of the RIS 100 (see FIG. 1), the configuration of the radiographic imaging room (see FIG. 2), the configuration of the electronic cassette 40 (see FIG. 3 to FIG. 5, FIG. 7, and FIG. 8), and the configuration of the imaging system 104 (see FIG. 9) described in the above exemplary embodiment are examples, and unnecessary portions can be omitted there from, new portions can be added thereto, and states of connection and so forth can be changed without departing from the gist of the present invention.

Further, the configuration of the angle-of-rotation information (FIG. 12) described in the above exemplary embodiment is also an example, and unnecessary information can be omitted therefrom and new information can be added thereto without departing from the gist of the present invention.

Further, the flows of processing by the various programs (see FIG. 13 and FIG. 15) described in the above exemplary embodiment are also examples, and unnecessary steps can be omitted therefrom, new steps can be added thereto, and the processing order can be switched around without departing from the gist of the present invention.

Further, the configuration of the initial information input screen (see FIG. 14) described in the above exemplary embodiment is also an example, and unnecessary information can be omitted therefrom and new information can be added thereto without departing from the gist of the present invention.

What is claimed is:

1. A radiographic image capturing system comprising:
    a radiographic image capturing device that comprises a radiation detector in which pixels having a sensitivity with respect to radiation or light into which radiation has been converted are disposed two-dimensionally at a predetermined pixel spacing, and that captures a radiographic image expressed by radiation applied to an imaging surface;
    a grid that is placed on a radiation source side of the radiation detector, the grid comprising absorbing members that are disposed at a predetermined spacing and absorb radiation;
    an acquiring unit that acquires an angle of inclination of the grid, with respect to an array direction of the pixels of the radiation detector, with which a spatial frequency of moiré fringes generated by the absorbing members of the grid in the radiographic image captured by the radiation detector is equal to or greater than a predetermined spatial frequency; and
    a processor that executes predetermined processing for making a relative angle between the grid and the radiation detector the acquired angle of inclination,
    wherein the predetermined spatial frequency is a spatial frequency of human body signals obtained by Fourier transforming, and mapping in a frequency space, a radiographic image representing a human body.

2. The radiographic image capturing system according to claim 1, wherein the spatial frequency of the human body signals is predetermined per site which is an imaging target of the radiographic image capturing device.

3. The radiographic image capturing system according to claim 1, wherein the acquiring unit acquires the angle of inclination by using a spatial frequency $f_G'$ obtained by the following expression and a ratio $\mu$ of an upper limit value $f_\mu$ of the spatial frequency of the human body signals with respect to the Nyquist frequency $f_N$ to calculate an angle $\theta$ that satisfies $f_G' > \mu f_N$:

$$f_{GX}' = \min(f_G \cos\theta - 2N_X f_N, 2(N_X+1)f_N - f_G \cos\theta)(N_X = [f_G \cos\theta/(2f_N)])$$

$$f_{GY}' = \min(f_G \sin\theta - 2N_Y f_N, 2(N_Y+1)f_N - f_G \sin\theta)(N_Y = [f_G \sin\theta/(2f_N)])$$

$$f_G' = \sqrt{f_{GX}'^2 + f_{GY}'^2} \qquad \text{[Expression]}$$

where $f_G$ is the number of lines, per 1 cm with respect to the array direction, of the absorbing members disposed in the grid, $f_N$ is the Nyquist frequency [lines/cm] defined by the pixel spacing of the radiation detector, and $\theta$ is the relative angle [degrees] between the grid and the radiation detector.

4. The radiographic image capturing system according to claim 1, further comprising a changing unit that changes a relative angle between the radiographic image capturing device and the grid,
    wherein the processor executes, as the predetermined processing, processing that controls the changing unit in such a way that the relative angle becomes the acquired angle of inclination.

5. The radiographic image capturing system according to claim 1, wherein the processor executes, as the predetermined processing, processing that provides notification of the acquired angle of inclination.

6. The radiographic image capturing system according to claim 1, further comprising:
    an identifying unit that identifies a spatial frequency of moiré fringes generated by the absorbing members in the radiographic image; and
    an image processing unit that performs image processing that removes, from the radiographic image, a component of the identified spatial frequency.

7. A radiographic image capturing system comprising:
    a radiographic image capturing device that comprises a radiation detector in which pixels having a sensitivity with respect to radiation or light into which radiation has been converted are disposed two-dimensionally at a predetermined pixel spacing, and that captures an image expressed by radiation applied to an imaging surface;
    an acquiring unit that acquires a type of a grid that is placed on a radiation source side of the radiation detector, and that comprises absorbing members which are disposed at a predetermined spacing and absorb radiation, and an angle of inclination of the grid, with respect to an array direction of the pixels of the radiation detector, that can make a spatial frequency of moiré fringes generated by the absorbing members of the grid in the radiographic image captured by the radiation detector equal to or greater than a predetermined spatial frequency; and
    a notifying unit that provides notification of the type and the angle of inclination of the grid acquired by the acquiring unit, wherein the predetermined spatial frequency is a spatial frequency of human body signals obtained by Fourier transforming, and mapping in a frequency space, a radiographic image representing a human body.

8. The radiographic image capturing system according to claim 7, wherein the acquiring unit acquires the type and the angle of inclination of the grid per site which is an imaging target of the radiographic image capturing device.

9. A non-transitory storage medium that stores a program that executes processing in a radiographic image capturing system including a radiographic image capturing device that comprises a radiation detector in which pixels having a sensitivity with respect to radiation or light into which radiation has been converted are disposed two-dimensionally at a predetermined pixel spacing, and that captures a radiographic image expressed by radiation applied to an imaging surface, and a grid that is placed on a radiation source side of the radiation detector, the grid comprising absorbing members that are disposed at a predetermined spacing and absorb radiation, the processing comprising:
- acquiring an angle of inclination of the grid, with respect to an array direction of the pixels of the radiation detector, with which a spatial frequency of moiré fringes generated by the absorbing members of the grid in the radiographic image captured by the radiation detector is equal to or greater than a predetermined spatial frequency; and
- executing predetermined processing for making a relative angle between the grid and the radiation detector the acquired angle of inclination,
- wherein the predetermined spatial frequency is a spatial frequency of human body signals obtained by Fourier transforming, and mapping in a frequency space, a radiographic image representing a human body.

10. The storage medium according to claim 9, wherein the spatial frequency of the human body signals is predetermined per site which is an imaging target of the radiographic image capturing device.

11. The storage medium according to claim 9, wherein the processing acquires the angle of inclination by using a spatial frequency $f_G'$ obtained by the following expression and a $\mu$ of an upper limit value $f_\mu$ of the spatial frequency of the human body signals with respect to the Nyquist frequency $f_N$ to calculate an angle $\theta$ that satisfies $f_G' > \mu f_N$:

$$f_{GX}' = \min(f_G \cos\theta - 2N_X f_N, 2(N_X+1)f_N - f_G \cos\theta)(N_X = [f_G \cos\theta/(2f_N)])$$

$$f_{GY}' = \min(f_G \sin\theta - 2N_Y f_N, 2(N_Y+1)f_N - f_G \sin\theta)(N_Y = [f_G \sin\theta/(2f_N)])$$

$$f_G' = \sqrt{f_{GX}'^2 + f_{GY}'^2} \quad \text{[Expression]}$$

where $f_G$ is the number of lines, per 1 cm with respect to the array direction, of the absorbing members disposed in the grid, $f_N$ is the Nyquist frequency [lines/cm] defined by the pixel spacing of the radiation detector, and $\theta$ is the relative angle [degrees] between the grid and the radiation detector.

12. The storage medium according to claim 9, wherein the predetermined processing includes controlling in such a way that a relative angle between the radiographic image capturing device and the grid becomes the acquired angle of inclination.

13. The storage medium according to claim 9, wherein the predetermined processing includes processing that provides notification of the acquired angle of inclination.

14. The storage medium according to claim 9, wherein the processing further comprises:
- identifying a spatial frequency of moiré fringes generated by the absorbing members in the radiographic image; and
- performing image processing that removes, from the radiographic image, a component of the identified spatial frequency.

15. The storage medium according to claim 9, wherein the processing further comprises acquiring a type of the grid.

16. The storage medium according to claim 15, wherein the processing comprises acquiring the type of the grid and the angle of inclination per site which is an imaging target of the radiographic image capturing device.

17. A method of operating a radiographic image capturing system including a radiographic image capturing device that comprises a radiation detector in which pixels having a sensitivity with respect to radiation or light into which radiation has been converted are disposed two-dimensionally at a predetermined pixel spacing, and that captures a radiographic image expressed by radiation applied to an imaging surface, and a grid that is placed on a radiation source side of the radiation detector, the grid comprising absorbing members that are disposed at a predetermined spacing and absorb radiation, the method comprising:
- acquiring an angle of inclination of the grid, with respect to an array direction of the pixels of the radiation detector, with which a spatial frequency of moiré fringes generated by the absorbing members of the grid in the radiographic image captured by the radiation detector is equal to or greater than a predetermined spatial frequency; and
- executing predetermined processing for making a relative angle between the grid and the radiation detector the acquired angle of inclination,
- wherein the predetermined spatial frequency is a spatial frequency of human body signals obtained by Fourier transforming, and mapping in a frequency space, a radiographic image representing, a human body.

18. A radiographic image capturing system comprising:
- a radiographic image capturing device that comprises a radiation detector in which pixels having a sensitivity with respect to radiation or light into which radiation has been converted are disposed two-dimensionally at a predetermined pixel spacing, and that captures a radiographic image expressed by radiation applied to an imaging surface;
- a grid that is placed on a radiation source side of the radiation detector, the grid comprising absorbing members that are disposed at a predetermined spacing and absorb radiation;
- an acquiring unit that acquires an angle of inclination of the grid, with respect to an array direction of the pixels of the radiation detector, with which a spatial frequency band of moiré fringes generated by the absorbing members of the grid in the radiographic image captured by the radiation detector is shifted in a direction away from a center position of a spatial frequency band of human body signals that are obtained by Fourier transforming, and mapping, in a frequency space, a radiographic image representing a human body; and
- a processor that executes predetermined processing for making a relative angle between the grid and the radiation detector the acquired angle of inclination.

* * * * *